(12) United States Patent
Meredith

(10) Patent No.: US 12,251,495 B2
(45) Date of Patent: Mar. 18, 2025

(54) BONE GRINDER PROMOTING BONE OSTEOINDUCTIVITY

(71) Applicant: Thomas Matthew Industries, Inc., Brentwood, TN (US)

(72) Inventor: Thomas L. Meredith, Brentwood, TN (US)

(*) Notice: Subject to any disclaimer, the term of this patent is extended or adjusted under 35 U.S.C. 154(b) by 0 days.

(21) Appl. No.: 18/532,697

(22) Filed: Dec. 7, 2023

(65) Prior Publication Data

US 2024/0252721 A1    Aug. 1, 2024

Related U.S. Application Data

(63) Continuation of application No. 18/215,030, filed on Jun. 27, 2023, now abandoned, which is a (Continued)

(51) Int. Cl.
   *B02C 18/22*     (2006.01)
   *A22C 17/06*     (2006.01)
   (Continued)

(52) U.S. Cl.
   CPC ....... *A61L 27/3691* (2013.01); *A61L 27/3608* (2013.01); *A61L 27/50* (2013.01);
   (Continued)

(58) Field of Classification Search
   CPC .. A61F 2/46; A61F 2002/4645; B02C 18/142; B02C 18/2291; B02C 2018/147;
   (Continued)

(56) References Cited

U.S. PATENT DOCUMENTS

| | | | |
|---|---|---|---|
| 2,044,563 | A | 6/1936 | Mitchell |
| 3,825,640 | A | 7/1974 | Maierson |

(Continued)

FOREIGN PATENT DOCUMENTS

| | | | |
|---|---|---|---|
| DE | 3610539 | A1 * | 10/1987 |
| KR | 20230022468 | A * | 2/2023 |
| WO | 2007091674 | A1 | 8/2007 |

OTHER PUBLICATIONS

Thomas Matthew Industries, Inc. Model ABG04, two photos including a picture of the single internal cutting element. This model was sold as early as 1992.

*Primary Examiner* — Jared O Brown
(74) *Attorney, Agent, or Firm* — Patterson Intellectual Property Law, P.C.; Ryan D. Levy

(57) ABSTRACT

A bone grinder may have a grinding chamber, an intermediate zone, and a primary cutting element and a secondary cutting element. The intermediate zone may have a first wall and a second wall within the grinding chamber, and the intermediate zone may separate the primary cutting element from the secondary cutting element. The first wall and the second wall may slope inward such that a distance between the first wall and the second wall generally decreases from the primary cutting element to the secondary cutting element. The primary cutting element and the secondary cutting element may be positioned within the grinding chamber to sequentially perform primary cutting operations and secondary cutting operations on a bone. A drive mechanism may operatively engage the primary cutting element and the secondary cutting element.

15 Claims, 15 Drawing Sheets

Related U.S. Application Data continuation of application No. 17/485,770, filed on Sep. 27, 2021, now abandoned.

(51) Int. Cl.
*A61F 2/46* (2006.01)
*A61L 27/36* (2006.01)
*A61L 27/50* (2006.01)
*B02C 18/06* (2006.01)
*B02C 18/08* (2006.01)
*B02C 18/14* (2006.01)
*B02C 18/16* (2006.01)
*B02C 18/18* (2006.01)
*B02C 19/00* (2006.01)

(52) U.S. Cl.
CPC .............. *B02C 18/06* (2013.01); *B02C 18/08* (2013.01); *B02C 18/142* (2013.01); *B02C 18/2291* (2013.01); *B02C 19/0056* (2013.01); *A22C 17/06* (2013.01); *A61F 2/4644* (2013.01); *A61F 2002/4645* (2013.01); *B02C 2018/147* (2013.01); *B02C 2018/162* (2013.01); *B02C 2018/188* (2013.01)

(58) Field of Classification Search
CPC ........ B02C 2018/162; B02C 2018/188; A22C 17/06; A61L 27/3608; A61L 27/3691; A61L 27/50
See application file for complete search history.

(56) References Cited

U.S. PATENT DOCUMENTS

| | | | |
|---|---|---|---|
| 3,852,045 A | 12/1974 | Wheeler et al. | |
| 3,975,479 A | 8/1976 | McClean | |
| 4,522,753 A | 6/1985 | Yannas et al. | |
| 4,645,503 A | 2/1987 | Lin et al. | |
| 4,678,470 A | 7/1987 | Nashef et al. | |
| 4,843,112 A | 6/1989 | Gerhart et al. | |
| 4,947,840 A | 8/1990 | Yannas et al. | |
| 5,061,286 A | 10/1991 | Lyle | |
| 5,439,684 A | 8/1995 | Prewett et al. | |
| 5,501,706 A | 3/1996 | Arenberg | |
| 5,507,813 A | 4/1996 | Dowd et al. | |
| 5,516,532 A | 5/1996 | Atala et al. | |
| 5,545,222 A | 8/1996 | Bonutti | |
| 5,565,502 A | 10/1996 | Glimcher et al. | |
| 5,607,269 A | 3/1997 | Dowd et al. | |
| 5,658,334 A | 8/1997 | Caldarise et al. | |
| 5,662,710 A | 9/1997 | Bonutti | |
| 5,824,078 A | 10/1998 | Nelson et al. | |
| 5,899,939 A | 5/1999 | Boyce et al. | |
| 5,906,322 A | 5/1999 | Hama | |
| 5,918,821 A | 7/1999 | Grooms et al. | |
| 6,025,538 A | 2/2000 | Yaccarino, III | |
| 6,045,554 A | 4/2000 | Grooms et al. | |
| 6,090,998 A | 7/2000 | Grooms et al. | |
| 6,123,731 A | 9/2000 | Boyce et al. | |
| 6,132,472 A | 10/2000 | Bonutti | |
| 6,136,029 A | 10/2000 | Johnson et al. | |
| 6,162,227 A | 12/2000 | Eckhardt et al. | |
| 6,187,329 B1 | 2/2001 | Agrawal et al. | |
| 6,210,031 B1 | 4/2001 | Murray | |
| 6,287,312 B1 | 9/2001 | Clokie et al. | |
| 6,294,187 B1 | 9/2001 | Boyce et al. | |
| 6,402,070 B1 | 6/2002 | Ishida et al. | |
| 6,464,156 B1* | 10/2002 | Wexell | A61F 2/4644 241/273.3 |
| 6,521,284 B1 | 2/2003 | Parsons et al. | |
| 6,755,365 B1* | 6/2004 | Meredith | A61F 2/4644 241/236 |
| 7,001,551 B2 | 2/2006 | Meredith | |
| 8,282,029 B2* | 10/2012 | Maaren | A22C 17/06 241/235 |
| 8,512,342 B2* | 8/2013 | Meredith | A61F 2/46 606/84 |
| 2003/0006327 A1* | 1/2003 | Ryu | B02C 18/142 241/236 |
| 2003/0083752 A1 | 5/2003 | Wolfinbarger, Jr. et al. | |
| 2003/0217415 A1 | 11/2003 | Crouch et al. | |
| 2009/0098092 A1 | 4/2009 | Meredith | |
| 2009/0157082 A1 | 6/2009 | Meredith | |
| 2012/0245703 A1 | 9/2012 | Meredith | |

\* cited by examiner

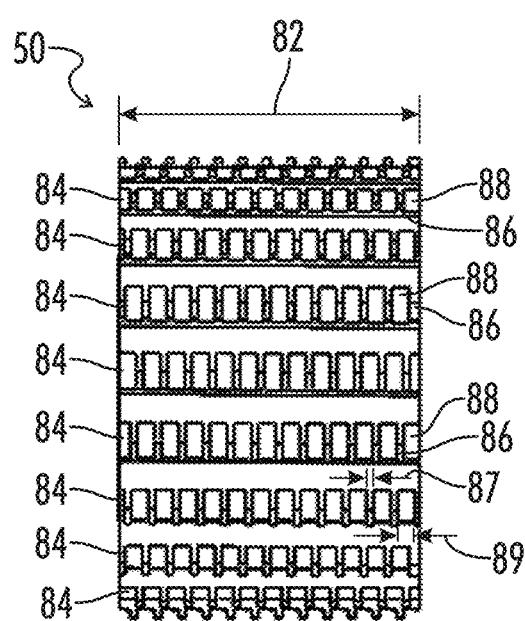
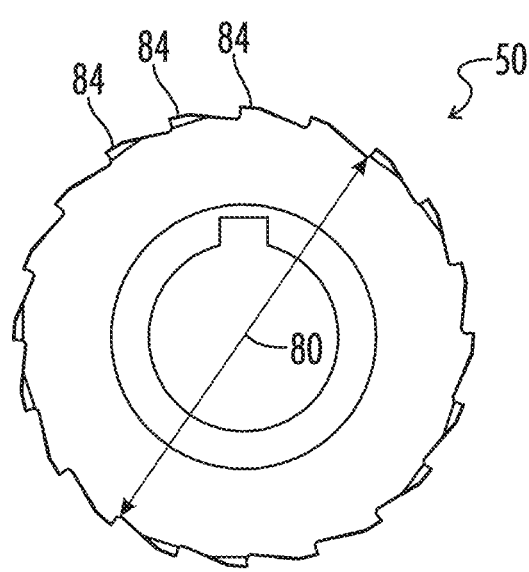
*FIG. 2A*  *FIG. 2B*

BONE GRINDER PROMOTING BONE OSTEOINDUCTIVITY

CROSS-REFERENCES TO RELATED APPLICATIONS

This application claims benefit of the following patent applications which are hereby incorporated by reference: U.S. patent application Ser. No. 17/485,770 filed Sep. 27, 2021; and U.S. patent application Ser. No. 18/215,030 filed Jun. 27, 2023.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

FIELD OF THE DISCLOSURE

The present disclosure relates generally to a bone grinder, and more particularly to a bone grinder promoting bone osteoinductivity.

BACKGROUND

There are many medical procedures requiring a donation of human organs and tissues. Bone is one of the required human tissues needed for a number of these medical procedures. Donated bone sample must first be processed into a bone matter or a bone particulate; thereafter, the bone matter or the bone particulate must then be demineralized. Among other uses and implementations, the bone matter or the bone particulate may be used in adhesives and/or in grafting material for bone-grafting operations, as well as in bone-tissue composites for the production of screws, disks, plates, pins, and joint sockets in connection with corrective or elective surgical procedures.

Several attempts have been made to manufacture, create, and/or produce bone grinding devices that mill the bone into usable bone matter or bone particulate, including U.S. Pat. Nos. 5,918,821 and 5,607,269. There are a number of drawbacks, however, associated with current models of bone grinding devices. First, current models of bone grinding devices necessitate a two-stage milling operation, which require at least two or more items or pieces of equipment. In a first of the at least two or more items or pieces of equipment, the bone is ground into intermediary pieces, or bone fragments; the intermediary pieces, or the bone fragments, are then physically transferred to a second of the at least two or more items or pieces of equipment to convert the intermediary pieces, or the bone fragments, into the bone matter or the bone particulate. While these current models of bone grinding devices may effectuate a milling operation on the bone, they nevertheless require a transfer of the bone between at least two or more items or pieces of equipment. Accordingly, the current models of bone grinding devices lack an efficient milling operation, conversion, and transformation of the bone into the bone matter or the bone particulate, whereby the milling operation is operated in an automated or near-automated manner, without interruptions or interferences to the conversion or transformation of the bone into the bone matter or the bone particulate.

A second drawback associated with current models of bone grinding devices is the likelihood of contamination of the bone during a milling operation on the bone. During the milling operation on the bone, it is generally imperative that the bone not be contaminated by external contaminants, including moisture, air, particulate matter, or other external environmental hazards. Accordingly, a sterilization of, or an increased sterilization in, the bone grinding device is instrumental in preserving the bio-integrity of the bone as it converts or transforms into the bone matter or the bone particulate. For example, in some models of the bone grinding devices, a motor or a drive mechanism of the bone grinding device may be in close, physical proximity to a discharge path of the processing section of the bone grinding device. Where the motor or drive mechanism is in close, physical proximity to the discharge path, the bone particulate or the bone matter may be contaminated by the air or particulate matter deriving from the motor or the drive mechanism. Accordingly, these models of the bone grinding devices fail to prevent, mitigate, or deter the contamination of the bone matter or the bone particulate, which is deleterious to the sterility and bio-integrity of the bone matter or the bone particulate in medical applications or surgical procedures.

In addition to issues of sterility in the bone particulate or the bone matter, a third drawback associated with current models of bone grinding devices is a collapse, degradation, diminution, or breakdown of morphogenetic proteins. Bone morphogenetic proteins, or "BMPs," are families of proteins that initiate, promote, and/or maintain morphogenesis. Morphogenesis is the development process through which the human organs and tissues acquire or achieve a physical shape or configuration that works in concert with human organs' and tissues' functions. Where there is the collapse, degradation, diminution, or breakdown of the morphogenetic proteins due to the conversion or transformation of the bone into the bone matter or the bone particulate, an osteoinductivity of the bone matter or the bone particulate may be reduced. Osteoinduction, to which the term "osteoinductivity" refers, is generally defined as a process by which osteogenesis is induced-bone is generated (or regenerated) from osteocompetent cells in bone connective tissue or bone cartilage. In other words, osteoinductivity of morphogenetic proteins refers to the ability or capacity for the morphogenetic proteins to generate (or regenerate) bone.

Osteoinductivity of the bone matter or the bone particulate may be degraded, diminished, or broken down through heat produced or dissipated in an operation of the bone grinding device. In current models of the bone grinding device, heat produced or dissipated during an operation of the bone grinding device may be unchecked or unregulated due to an absence of an automated process that regulates a speed of cutting elements in the bone grinding device. Heat produced or dissipated during the operation of the bone grinding device may be further unchecked or unregulated due to an inconsistent or increased pressure and rate at which the bone may be fed into the cutting elements of the bone grinding device. Moreover, in current models of the bone grinding device, the cutting elements may continue to be engaged by the motor or the drive mechanism after the bone has been transformed or converted into the bone matter and/or the bone particulate. Where the cutting elements continue to function after the bone has been transformed or converted into the bone matter and/or the bone particulate, unnecessary heat is generated by the operation of the cutting elements, thereby further degrading, diminished, or otherwise breaking down the osteoinductivity of the bone matter and/or the bone particulate.

Current models of bone grinding devices may further adversely affect the osteoinductivity of the bone or lead to an inefficient milling of the bone due to the presence of a "bone swirling" effect. The "bone swirling" effect occurs where the bone is not efficiently milled by the cutting elements, thereby leaving the bone particulate or bone matter not usable in medical application or surgical procedures. For example, in U.S. Pat. No. 6,755,365, a bone grinder is disclosed, wherein the bone grinder is automated and sterilely processes bone into the bone matter or the bone particulate for use in medical procedures or surgical operations. In U.S. Pat. No. 6,755,365, the bone grinder of the disclosure comprises a grinding chamber and primary and secondary cutting elements positioned with the grinding chamber to sequentially perform primary and secondary cutting operations on the bone. While the bone grinder disclosed in U.S. Pat. No. 6,755,365 is efficient in converting or transforming bone into the bone matter or the bone particulate, the bone grinder of the foregoing disclosure may inadvertently promote or initiate the "bone swirling" effect, whereby the bone matter or the bone particulate, as it moves from the primary cutting element to the secondary cutting element, either does not transfer to the secondary cutting element, and further to the discharge path, or the bone matter or the bone particulate moves in a "swirling" motion in an intermediate space between the primary cutting element and the secondary cutting element. By having the bone particulate or the bone matter "swirl" in the intermediate space or not transfer to the secondary cutting element, the bone grinding device is prevented or delayed from efficiently transforming or converting the bone into the bone matter or the bone particulate. And, where the bone grinding device is delayed from efficiently transforming or converting the bone into the bone matter or the bone particulate, unnecessary heat may be generated or dissipated in the grinding chamber, the heat of which degrades, diminishes, decreases, or breaks down the osteoinductivity of the bone.

Other current models of bone grinding devices may diminish, decrease, or break down the osteoinductivity of the bone or lead to an inefficient milling of the bone where the cutting elements are unable to effectuate uninhibited or unobstructed shearing, grinding, or slicing forces on and against the bone. For example, in U.S. Pat. No. 8,512,342, a portable bone grinder is disclosed wherein two or more cutting heads perform cutting operations on the bone to produce the bone matter or the bone particulate. Among other features, the portable bone grinder of U.S. Pat. No. 8,512,342 discloses one or more scrappers, wherein the one or more scrappers may facilitate or enable a removal of "stuck," "lodged," or "adhered" bone matter or bone particulate from the two or more cutting heads. While the bone grinder disclosed in U.S. Pat. No. 8,512,342 is efficient in converting or transforming bone into the bone matter or the bone particulate with requisite sterility, the one or more scrappers must be withdrawn from the portable grinder by a user to use the one or more scrappers to remove the "stuck," "lodged," or "adhered" bone matter or bone particulate. Accordingly, current models of bone grinding devices, including the disclosure of U.S. Pat. No. 8,512,342, lack an automated process of discharging the "stuck" bone matter or bone particulate, so as to not interrupt or interfere with the milling operation of the bone grinder. Where the bone grinding device is unable to effectively shear, grind, or slice the bone, so as to convert or transform the bone into the bone matter or the bone particulate, unnecessary heat may be generated or dissipated, which in turn, further diminishes, decreases, or breaks down the osteoinductivity of the bone.

Thus, current models of bone grinding devices present at least the following problems: current models of bone grinding devices lack an efficient milling operation and conversion or transformation of the bone to the bone matter or bone particulate, due at least in part to interruptions or interferences with the grinding, slicing, and/or shearing of the bone; the bone is likely to be exposed to environmental contaminants during a milling operation on the bone, thereby adversely impacting the sterility requirements for use in medical procedures or surgical operations; and unnecessary heat is generated or dissipated by an inefficient milling of the bone, including the "bone swirling" effect and/or the adherence of the bone matter or the bone particulate to the cutting elements of the bone grinding devices. Accordingly, there is a need to provide a bone grinder that overcomes the foregoing limitations associated with current models of the bone grinding devices and inefficiencies therein.

BRIEF SUMMARY

The present disclosure provides a novel bone grinder. Specifically, the present disclosure provides a novel bone grinder promoting osteoinductivity.

In light of the drawbacks associated with current models of bone grinding devices, it would be desirable to provide a novel bone grinder that overcomes at least the foregoing limitations. The present disclosure provides various embodiments of a bone grinder, each of the various embodiments of the bone grinder having elements or features that improve a functionality of the bone grinding devices or otherwise promote, improve, or increase an osteoinductivity of the bone as the bone is milled, transformed, and/or converted from bone into bone matter or bone particulate, such as bone fragments and/or bone powder. In accordance with the present disclosure, an embodiment of the bone grinder is provided, wherein the bone grinder may include an intermediate zone having a first wall and a second wall. The intermediate zone may be positioned within a grinding chamber and may separate a primary cutting element from a secondary cutting element. A distance between the first wall and the second wall may generally decrease from the primary cutting element to the secondary cutting element. The distance between the first wall and second wall may reduce, mitigate, or prevent a "bone swirling" effect, permitting a bone to be efficiently milled from the primary cutting element to the secondary cutting element.

In accordance with the present disclosure, another embodiment of the bone grinder is provided, wherein the bone grinder may include a primary cutting element positioned within a grinding chamber to perform primary cutting operations on a bone to convert or transform bone into bone matter or bone particulate, such as bone fragments and/or bone powder. The primary cutting element may include one or more primary cutting tools with primary cutting teeth, each having a row of alternating recesses and ridges. One or more rakes, which are positioned within the grinding chamber and after the primary cutting element, may have raking teeth with a row of alternating recesses and ridges corresponding to the alternating recesses and ridges of the primary cutting teeth. The correspondence between the primary cutting teeth and the raking teeth may facilitate a removal of "stuck," "lodged," or "adhered" bone matter or bone particulate from the primary cutting element. Accordingly, the disclosure herein may provide an automated process of discharging the "stuck" bone matter or bone particulate, so as to not interrupt or interfere with the milling operation of the bone grinder, and not generate or dissipate unnecessary heat through inefficient and continued operation of the primary cutting element.

In accordance with the present disclosure, an alternative embodiment of the bone grinder is provided, wherein the bone grinder includes a primary cutting element positioned within a grinding chamber to perform primary cutting operations on a bone to convert or transform bone into bone matter or bone particulate, such as bone fragments and/or bone powder. The primary cutting element may include one or more primary cutting tools with primary cutting teeth, each having a row of alternating recesses and ridges. A scraper may be positioned within the grinding chamber and positioned proximate to the primary cutting tool, such that a scraping edge of the scraper may apply a shearing or shaving force against the primary cutting teeth. By applying the shearing or shaving force against the primary cutting teeth, the scraper may facilitate a removal of "stuck," "lodged," or "adhered" bone matter or bone particulate from the primary cutting element. Accordingly, the disclosure herein may provide an automated process of discharging the "stuck" bone matter or bone particulate, so as to not interrupt or interfere with the milling operation of the bone grinder and not generate or dissipate unnecessary heat through inefficient and continued operation of the primary cutting element.

In accordance with the present disclosure, a further embodiment of the bone grinder is provided, wherein the bone grinder may include a chute configured to contain and guide a bone to a grinding chamber. A primary cutting element may be located within the grinding chamber to perform primary cutting operations on the bone to convert or transform the bone into bone matter or bone particulate, such as bone fragments or bone powder. A push platform may be located within the chute and operable between a compressed position and a released position. In the compressed position, a drive mechanism may operatively engage the primary cutting element for when the chute at least contains the bone, and in the released position, the drive mechanism may operatively disengage the primary cutting element from performing the primary cutting operations for when the chute does not at least contain the bone. The push platform may prohibit or deter an inefficient milling operation of the bone grinder, wherein unnecessary heat may be generated or dissipated due to attenuated or extended engagement by the drive mechanism when the bone has been converted or transformed from the bone into the bone matter or the bone particulate, such as bone fragments or bone powder.

In the context of a bone grinder, the bone grinder having a grinding chamber, an intermediate zone, and a primary cutting element and a secondary cutting element is provided herein. The intermediate zone may have a first wall and a second wall within the grinding chamber, and the intermediate zone may separate the primary cutting element from the secondary cutting element. The first wall and the second wall may slope inward such that a distance between the first wall and the second wall generally decreases from the primary cutting element to the secondary cutting element. The primary cutting element and the secondary cutting element may be positioned within the grinding chamber to sequentially perform primary cutting operations and secondary cutting operations on a bone. A drive mechanism may operatively engage the primary cutting element and the secondary cutting element.

In the context of a bone grinder, the bone grinder having a grinding chamber, a primary cutting element, and one or more rakes is provided herein. The primary cutting element may be located within the grinding chamber to perform primary cutting operations on a bone to produce bone matter. The primary cutting element may be operatively engaged by a drive mechanism. The primary cutting element may have one or more primary cutting tools, each of the one or more primary cutting tools having primary cutting teeth. The primary cutting teeth may have a row of alternating recesses and ridges. The bone grinder may further include one or more rakes, each of the one or more rakes having raking teeth. The raking teeth may include a row of alternating recesses and ridges. One of the one or more rakes may be positioned within the grinding chamber and after the primary cutting element, such that row of alternating recesses and ridges of the primary cutting teeth of one of the one or more primary cutting tools may correspond with the row of alternating recesses and ridges of the raking teeth of the one of the one or more rakes.

In the context of a bone grinder, the bone grinder having a chute, a grinding chamber, a primary cutting element, and a push platform is provided herein. The chute may be positioned before the grinding chamber and may be configured to contain and guide a bone to the grinding chamber. The grinding chamber may contain the primary cutting element, and the primary cutting element may perform primary cutting operations on the bone to produce matter. The primary cutting element may be operatively engaged by a drive mechanism. The chute may contain a push platform, and the push platform may be operable between a compressed position and a released position. The compressed position may be configured to enable the drive mechanism to operatively engage the primary cutting element where the chute contains the bone to be guided to the grinding chamber. The released position may be configured to operatively disengage the primary cutting element from performing the primary cutting operations for when the chute does not contain the bone to be guided to the grinding chamber.

In one particular and exemplary embodiment, a bone grinder is provided, wherein the bone grinder has a grinding chamber, an intermediate zone, a primary cutting element, and a secondary cutting element. The intermediate zone has a first wall and a second wall within the grinding chamber, and the intermediate zone separates the primary cutting element from the secondary cutting element. The first wall and the second wall of the intermediate zone slope inward such that a distance between the first wall and the second wall generally decreases from the primary cutting element to the secondary cutting element. The primary cutting element and the secondary cutting element are positioned within the grinding chamber to sequentially perform primary cutting operations and secondary cutting operations on a bone. The primary cutting element and the secondary cutting element are operatively engaged by a drive mechanism.

In one aspect according to the above-referenced embodiment, the first wall and the second wall of the intermediate zone may be sloped inward in a generally linear manner.

In another embodiment, the first wall and the second wall of the intermediate zone may be sloped inward in a generally curved manner.

In another embodiment, the intermediate zone may occupy a volume within the grinding chamber that is between about 2.5 in$^3$ and about 13 in$^3$.

In another embodiment, the bone grinder may further include a chute and a discharge path. The chute may be positioned before the grinding chamber, and the chute may be configured to contain and direct the bone to the grinding chamber. The discharge path may be positioned after the grinding chamber, and the discharge path may be configured to dispense the bone as bone matter.

In one aspect according to the above-referenced embodiment, the primary cutting element may have a primary first end opposite to a primary second end, such that the primary first end may be adjacent to the chute and the primary second end may be adjacent to the intermediate zone. The secondary cutting element may have a secondary first end opposite to a secondary second end, the secondary first end adjacent to the intermediate zone and the secondary second end adjacent to the discharge path. The primary second end of the primary cutting element may have a distance between about 0.75 inches to about 3 inches from the secondary first end of the secondary cutting element.

In another embodiment, the secondary cutting element may include a first cutting tool and a second cutting tool.

In one aspect according to the above-referenced embodiment, the first cutting tool may have a first set of teeth and a second cutting tool may have a second set of teeth. The first cutting tool and the second cutting tool may be positioned to define a cutting zone between the first set of teeth and the second set of teeth.

In one aspect according to the above-referenced embodiment, the first set of teeth of the first cutting tool are positioned within the cutting zone to alternate with and overlap with the second set of teeth of the second cutting tool.

In another embodiment, the first set of teeth of the first cutting tool may move in a first direction through the cutting zone and the second set of teeth of the second cutting tool may move in a second direction through the cutting zone, such that the first direction and the second direction are similar.

In another embodiment, the first set of teeth of the first cutting tool may move in a first direction through the cutting zone and the second set of teeth of the second cutting tool may move in a second direction through the cutting zone, such that the first direction and the second direction are different.

In one particular and exemplary embodiment, a bone grinder is provided, wherein the bone grinder includes a grinding chamber, a primary cutting element, and one or more rakes. The primary cutting element is located within the grinding chamber, and the primary cutting element performs primary cutting operations on a bone to produce bone matter. The primary cutting element is operatively engaged by a drive mechanism. The primary cutting element has one or more primary cutting tools, each of the one or more primary cutting tools having a row of alternating recesses and ridges. The one or more rakes have raking teeth, the raking teeth having a row of alternating recesses and ridges. One of the one or more rakes are positioned within the grinding chamber and after the primary cutting element. The row of alternating recesses and ridges of the primary cutting teeth of one of the one or more primary cutting tools corresponds with the row of alternating recesses and ridges of the raking teeth of the one of the one or more rakes.

In one aspect according to the above-referenced embodiment, the bone grinder may further include a secondary cutting element positioned within the grinding chamber, such that the primary cutting element and the secondary cutting element may sequentially perform the primary cutting operations and secondary cutting operations on the bone to produce the bone matter. The primary cutting element and the secondary cutting element may be operatively engaged by the drive mechanism.

In one aspect according to the above-referenced embodiment, the secondary cutting element may have a first secondary cutting tool and a second secondary cutting tool. The first secondary cutting tool may have a first set of secondary cutting teeth and the second secondary tool may have a second set of secondary cutting teeth. The first set and the second set of the secondary teeth may have a row of alternating recesses and ridges.

In one aspect according to the above-referenced embodiment, the one of the one or more rakes and a second of the one or more rakes within the grinding chamber are positioned after the secondary cutting element, such that the row of alternating recesses and ridges of the first set and the second set of secondary cutting teeth respectively correspond with the row of alternating recesses and ridges of the raking teeth of the one of the one or more rakes and the second of the one or more rakes, whereby the raking teeth are configured to remove bone matter from the secondary cutting teeth during concurrent movement of the first and second secondary cutting tool.

In another embodiment, the first secondary cutting and the second secondary cutting tool may be positioned to define a cutting zone between the first set of secondary teeth and the second set of secondary teeth. The first set of secondary teeth of the first secondary cutting tool may be positioned within the cutting zone to alternate with and overlap with the second set of secondary teeth of the second secondary cutting tool.

In one aspect according to the above-referenced embodiment, the first set of secondary teeth of the first secondary cutting tool may move in a first direction through the cutting zone and the second set of the secondary teeth of the second secondary cutting tool may move in a second direction through the cutting zone. The first direction and the second direction may be similar.

In another embodiment, the first set of secondary teeth of the first secondary cutting tool may move in a first direction through the cutting zone and the second set of the secondary teeth of the second secondary cutting tool may move in a second direction through the cutting zone. The first direction and the second direction may be different.

In one particular and exemplary embodiment, a bone grinder having a chute, a grinding chamber, a primary cutting element, and a push platform is provided herein. The chute is positioned before the grinding chamber and is configured to contain and guide a bone to the grinding chamber. A primary cutting element is located within the grinding chamber to perform primary cutting operations on the bone to produce bone matter. The primary cutting element is operatively engaged by a drive mechanism. The chute contains the push platform. The push platform is operable between a compressed position and a released position. The compressed position is configured to enable the drive mechanism to operatively engage the primary cutting element for when the chute contains the bone to be guided to the grinding chamber. The released position is configured to operatively disengage the primary cutting element from performing primary cutting operations for when the chute does not contain the bone to be guided to the grinding chamber.

In one aspect according to the above-referenced embodiment, a secondary cutting element may be positioned within the grinding chamber. The primary cutting element and the secondary cutting element may sequentially perform the primary cutting operations and secondary cutting operations on the bone to produce the bone matter. The primary cutting element and the secondary cutting element may be operatively engaged by the drive mechanism.

In one aspect according to the above-referenced embodiment, the released position of the push platform may operatively disengage the primary cutting element and the secondary cutting element from sequentially performing the primary cutting operations and the secondary cutting operations.

In another embodiment, the primary cutting element may include a first primary cutting tool and a second primary cutting tool. The first primary cutting tool may include a first set of primary cutting teeth and the second cutting tool may include a second set of primary cutting teeth. The first primary cutting tool and the second primary cutting tool may be positioned to define a cutting zone between the first set of primary cutting teeth and the second set of primary cutting teeth.

In one aspect according to the above-referenced embodiment, the first set of primary cutting teeth of the first primary cutting tool may be positioned within the cutting zone to alternate with and overlap with the second set of primary cutting teeth of the second primary cutting tool.

In another embodiment, the first set of primary cutting teeth of the first primary cutting tool may move in a direction through the cutting zone and the second set of primary cutting teeth of the second primary cutting tool may move in a second direction through the cutting zone. The first direction and the second direction may be similar.

In another embodiment, the first set of primary cutting teeth of the first primary cutting tool may move in a direction through the cutting zone and the second set of primary cutting teeth of the second primary cutting tool may move in a second direction through the cutting zone. The first direction and the second direction may be different.

In another embodiment, the chute may be configured to receive a bone supplying rod, and the bone supplying rod may be configured to direct the bone to the grinding chamber.

In one aspect according to the above-referenced embodiment, the bone supplying rod may direct the bone to the grinding chamber, such that the push platform may be operated to the compressed position.

In another embodiment, the bone supplying rod may not direct the bone to the grinding chamber and the bone supplying rod may be at least partially withdrawn from the chute, such that the push platform is operated to the released position.

In another embodiment, the push platform may include a reed switch, such that the reed switch is configured to operatively disengage the primary cutting element from performing primary cutting operations where the push platform is operated to the released position.

Unless otherwise defined, all technical and scientific terms used herein have the same meaning as commonly understood by one of ordinary skill in the art to which this invention belongs. The present invention may be embodied in other specific forms without departing from the spirit or essential attributes thereof, and it is therefore desired that the present embodiment be considered in all aspects as illustrative and not restrictive. Any headings utilized in the description are for convenience only and no legal or limiting effect. Numerous objects, features, and advantages of the embodiments set forth herein will be readily apparent to those skilled in the art upon reading of the following disclosure when taken in conjunction with the accompanying drawings.

BRIEF DESCRIPTION OF THE DRAWINGS

FIG. 2A is a side view of a coarse cutting tool to be positioned within a grinding chamber of an embodiment of a bone grinder.
FIG. 2B is a front view of the coarse cutting tool to be positioned within the grinding chamber of the embodiment of the bone grinder.

DETAILED DESCRIPTION

Figure 1A:
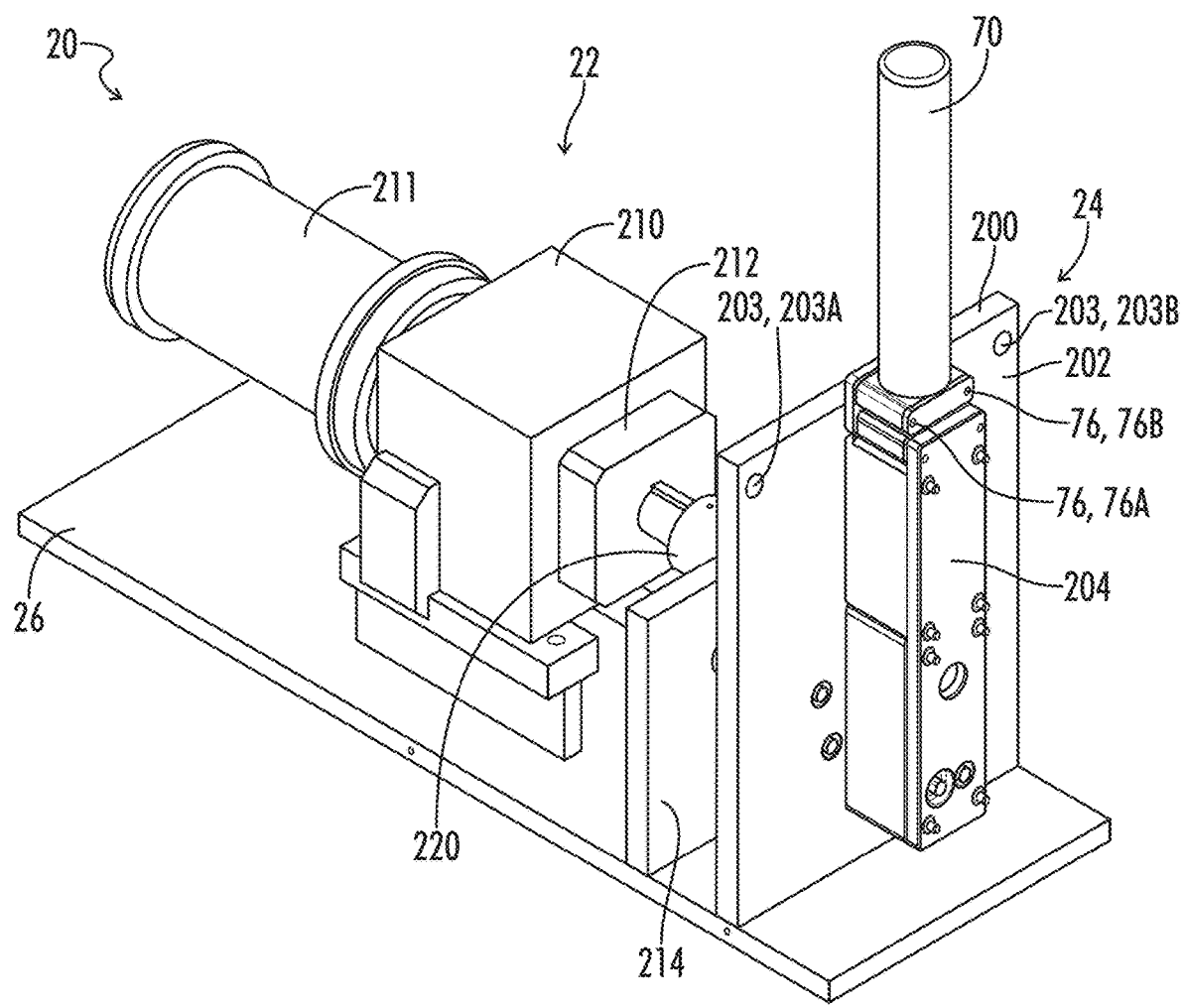
FIG. 1A is a perspective view of an embodiment of a bone grinder having a drive section and a processing section.

Reference will now be made in detail to embodiments of the present disclosure, one or more drawings of which are set forth herein. Each drawing is provided by way of explanation of the present disclosure and is not a limitation. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

Thus, it is intended that the present disclosure covers such modifications and variations as come within the scope of the appended claims and their equivalents. Other objects, features, and aspects of the present disclosure are disclosed in, or are obvious from, the following detailed description. It is to be understood by one of ordinary skill in the art that the present discussion is a description of exemplary embodiments only and is not intended as limiting the broader aspects of the present disclosure.

The words "connected," "attached," "joined," "mounted," "fastened," "fixed," "engaged," and the like, or any variation thereof, should be interpreted to mean any manner of joining two objects including, but not limited to, the use of any fasteners such as screws, nuts and bolts, bolts, pin and clevis, and the like allowing for a stationary, translatable, or pivotable relationship; welding of any kind such as traditional MIG welding, TIG welding, friction welding, brazing, soldering, ultrasonic welding, torch welding, inductive welding, and the like; using any resin, glue, epoxy, and the like; being integrally formed as a single part together; any mechanical fit such as a friction fit, interference fit, slidable fit, rotatable fit, pivotable fit, and the like; any combination thereof; and the like.

Referring to FIGS. 1A-6C, various embodiments may now be described of a bone grinder 20 having a grinding chamber 30, a chute 32, and a discharge path 34. More particularly, in referring to FIGS. 1A-6C, various embodiments may now be described of the bone grinder 20 having one or more cutting elements, including a primary cutting element 40 and/or a secondary cutting element 42, positioned or located within the grinding chamber 30. Similarly, in referring to FIGS. 1A-6C, various embodiments may now be described of the bone grinder 20 having one or more cutting tools, including a coarse cutting tool 50 and/or a fine cutting tool 52. For the purpose of the disclose herein, the primary cutting element 40, which performs a primary cutting operation on a bone 10, may include either the coarse cutting tool 50 or the fine cutting tool 52. In other words, where the disclosure refers to the primary cutting element 40, the primary cutting element 40 may be any one of the one or more cutting tools, including the coarse cutting tool 50 or the fine cutting tool 52, that perform the primary cutting operation on the bone 10. The primary cutting operation may convert or transform the bone 10 to bone matter 12, either as bone fragments 14 or bone powder 16. Moreover, for the purpose of the disclosure herein, the secondary cutting element 42, which performs a secondary cutting operation on the bone 10, may include either the coarse cutting tool 50 or the fine cutting tool 52. In other words, where the disclosure refers to the secondary cutting element 42, the secondary cutting element 42 may be any one of the one or more cutting tools, including the coarse cutting tool 50 or the fine cutting tool 52, that perform the secondary cutting operation on the bone 10. The secondary cutting operation may convert or transform the bone 10 to the bone matter 12, either as the bone fragments 14 or the bone powder 16. In optional embodiments, the primary cutting element 40 may include the coarse cutting tool 50 and the secondary cutting element 42 may include the fine cutting tool 52, and in other optional embodiments, the primary cutting element 40 may include the fine cutting tool 52. The bone grinder 20 need not include the secondary cutting element 42 where the primary cutting element 40 is positioned or located within the grinding chamber 30; and, in optional embodiments where there is no secondary cutting element 42 positioned or located within the grinding chamber 30, the primary cutting element 40 may be the coarse cutting tool 50 or the fine cutting tool 52.

Referring to FIGS. 1A-1E, an embodiment of the bone grinder 20 is disclosed. The bone grinder 20 may be formed by a material, the material including at least one of steel, plastic-based, FDA-approved material, ceramic, or any other variety or alloys, metals, or polymers which may provide a firm and rigid structure for the bone grinder 20. The bone grinder 20 may be described as having at least two sections, a drive section 22 and a processing section 24. In optional embodiments, the drive section 22 and the processing section 24 of the bone grinder 20 may rest upon, or be affixed or mounted to, a support member 26, or a support board 26 or support plate 26. The support member 26 may enable a user of the bone grinder 20 to portably move or transport the bone grinder 20, either with or without casters (not shown), between a bone-tissue processing room and/or a surgical suite or medical-operation facility.

The processing section 24 may include the grinding chamber 30 and one or more cutting elements positioned within the grinding chamber 30, such as the primary cutting element 40 and/or the secondary cutting element 42. The primary cutting element 40 and/or the secondary cutting element 42 may perform the primary cutting operations or the secondary cutting operations on the bone 10, respectively. The drive section 22 may include a drive mechanism 212 operatively engaging the one or more cutting elements, including the primary cutting element 40 and/or the secondary cutting element 42.

The drive section 22 may be engaged to the processing section 24 through one or more drive shafts 216. The one or more drive shafts 216 may be engaging the drive section 22 to the processing section 24 by and through a mounting, fixing, and/or stabilizing of the one or more drive shafts 216 onto a drive plate 214. In optional embodiments, the drive section 22 may include a first drive shaft 216A, a second drive shaft 216B, a third drive shaft 216C, and a fourth drive shaft 216D. For the purpose of the disclosure herein, any reference to the one or more drive shafts 216 may constitute the first drive shaft 216A, the second drive shaft 216B, the third drive shaft 216C, and/or the fourth drive shaft 216D. The one or more drive shafts 216 may be supported by a bearing (not shown) that further facilitates an environmental separation of the drive mechanism 212 of the drive section 22 from the processing section 24.

The drive mechanism 212 may be a mechanical drive mechanism that is either (or both) electrically powered or pneumatically powered. The drive mechanism 212 may convert electrical energy or pneumatic energy into mechanical energy for milling the bone 10 into the bone matter 12, either (or both) as the bone fragments 14 and/or the bone powder 16. A motor 211 facilitating the mechanical drive mechanism, whether enabled by electricity or compressed air, may have a power measurement of between about three (3) to four (4) horsepower (HP). In optional embodiments where the motor 211 is enabled by compressed air, operational pressure may range from about twenty (20) pounds per square inch (psi) and higher; in other optional embodiments, operational pressure may range from about forty (40) pounds per square inch (psi) and higher. In optional embodiments, where the motor 211 is enabled by electricity, the motor 211 may have a power measurement of about four (4) horsepower (HP) and may operate at 110/120 volts (V), although the motor 211 may be designed for additional or different electronic inputs. The drive mechanism 212 of the drive section 22 may be housed or stored within, or adjacent to, a control box 210, which may be formed by a material including stainless steel, metal, metallic alloys, various polymers, and combinations thereof. The control box 210 may include various electronic controls (not shown) for operating the bone grinder 20, including a programmable logic controller (PLC).

Figure 1B:
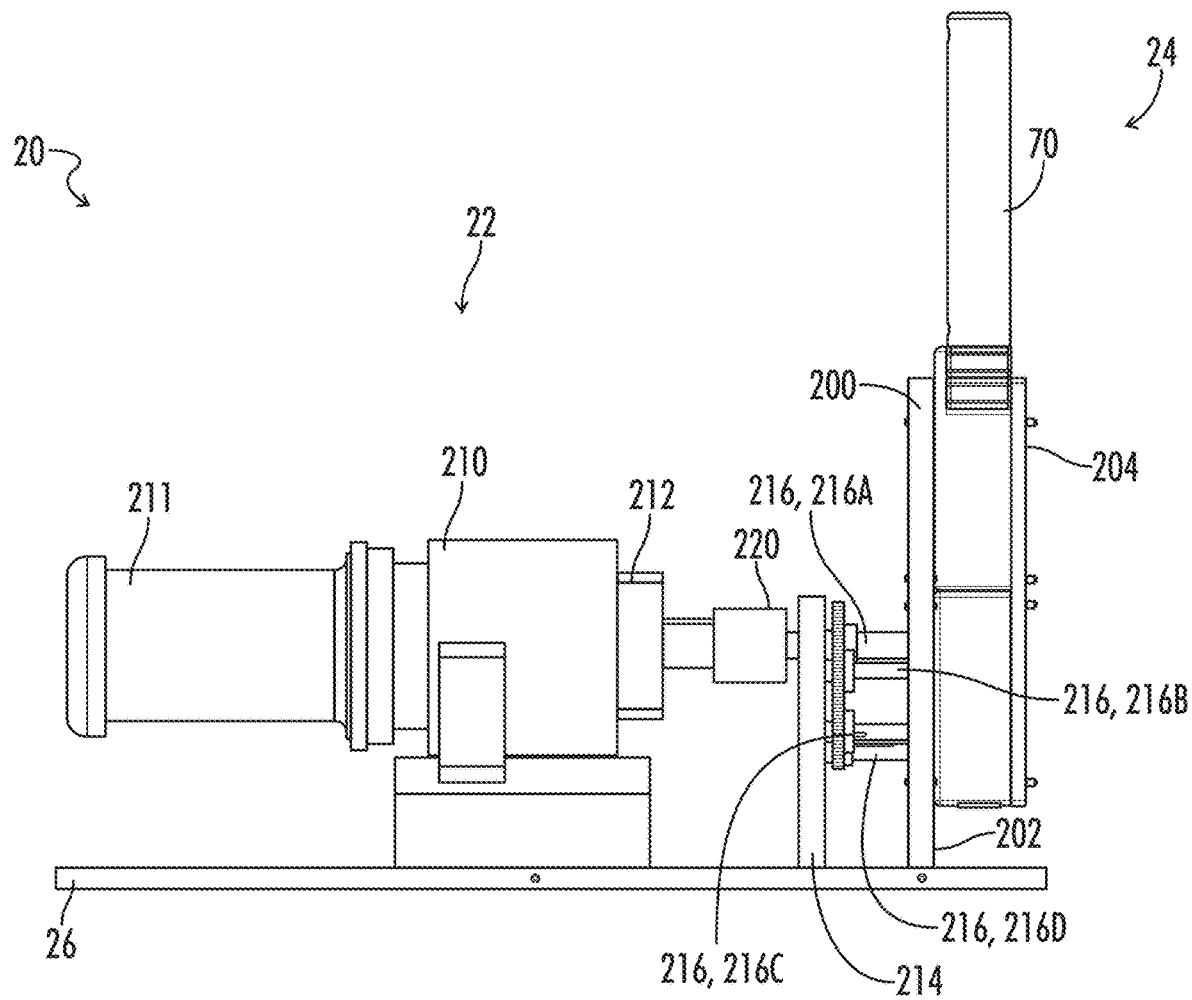
FIG. 1B is a side view of the embodiment of the bone grinder having the drive section and the processing section.
Figure 1C:
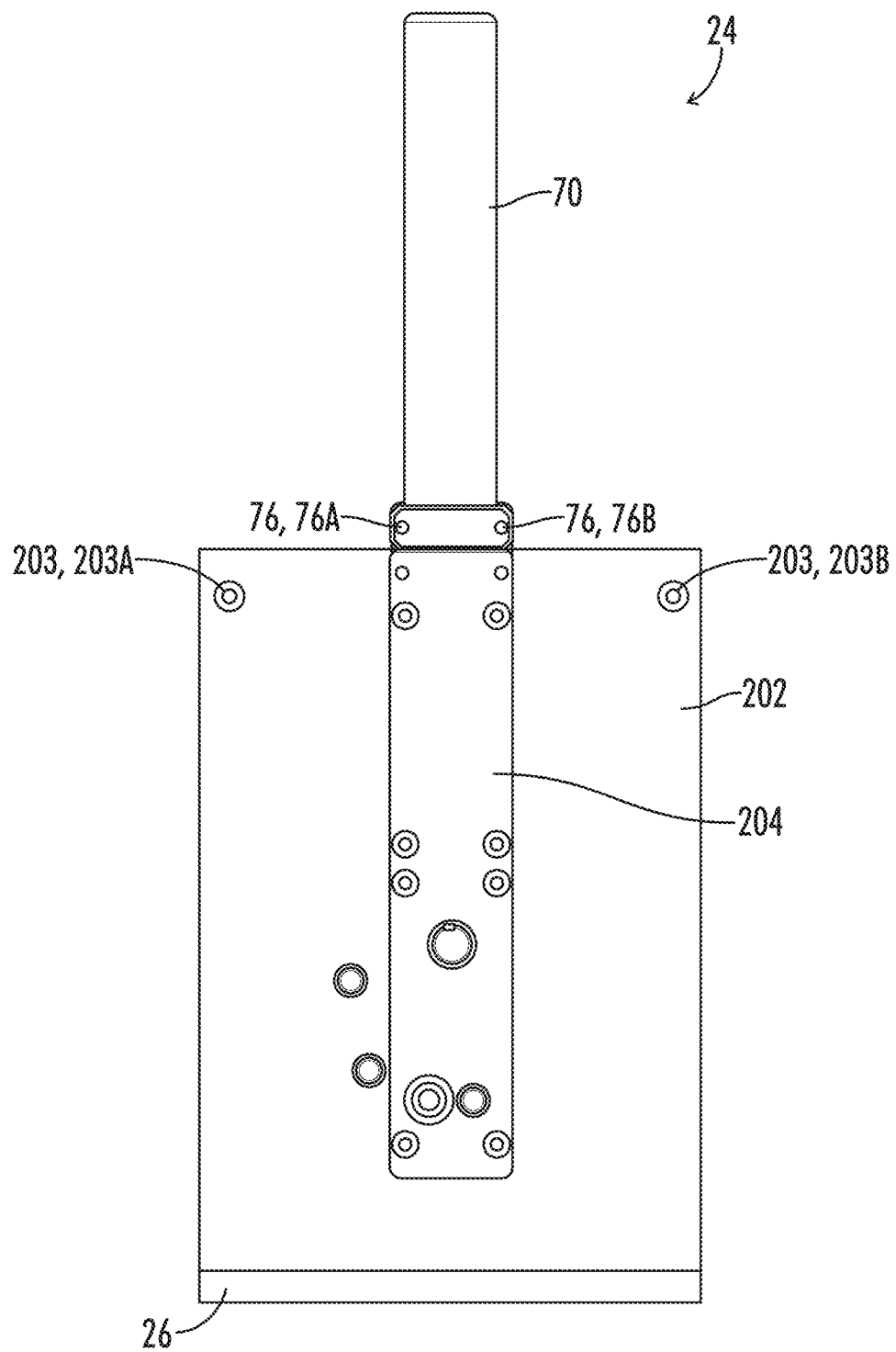
FIG. 1C is a front view of the embodiment of the bone grinder with a front plate covering a chute, a grinding chamber, and a discharge path of the processing section.
Figure 1D:
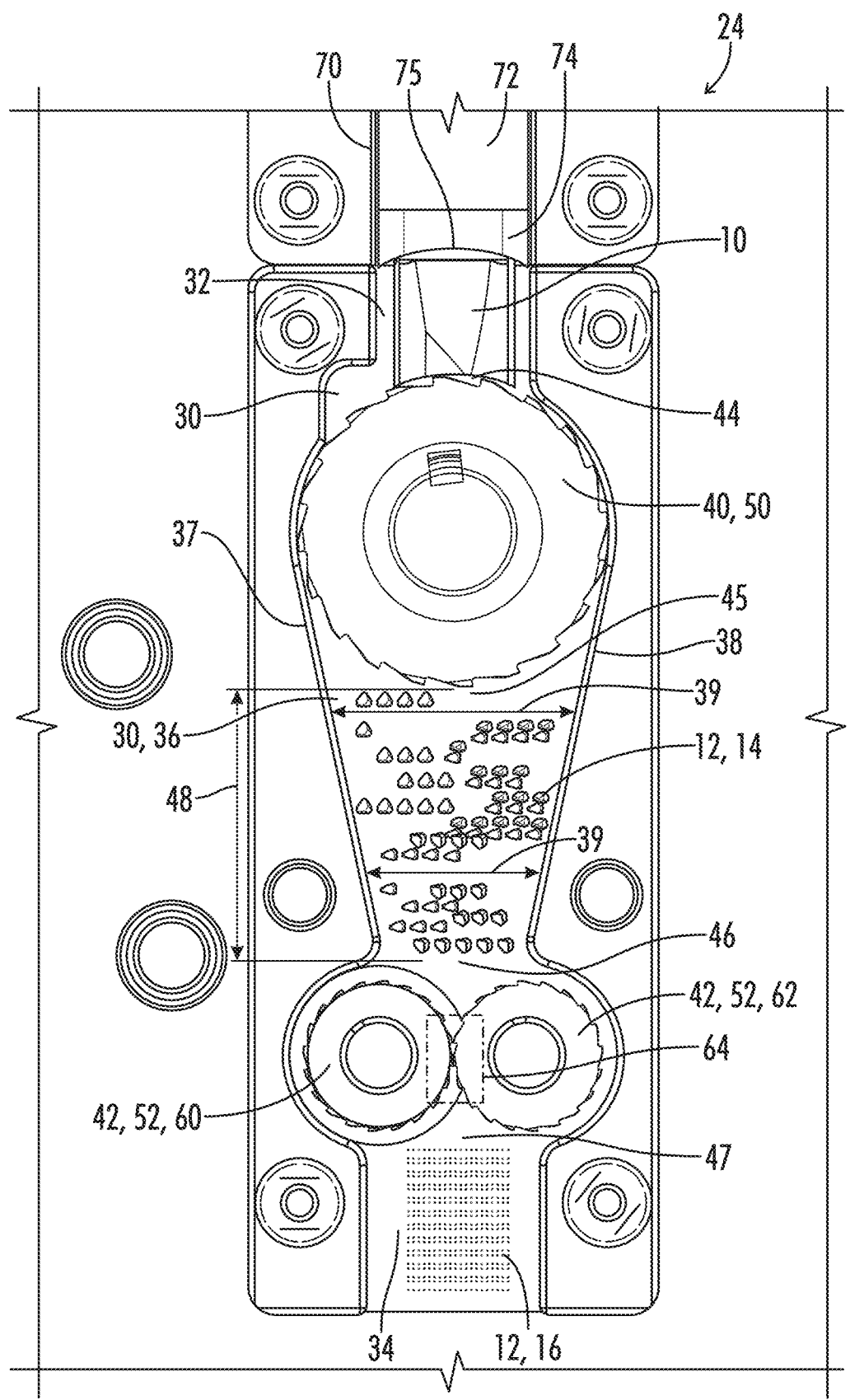
FIG. 1D is a front view of the embodiment of the bone grinder with the front plate removed conveying the chute, the grinding chamber, and the discharge path of the processing section.
Figure 1E:
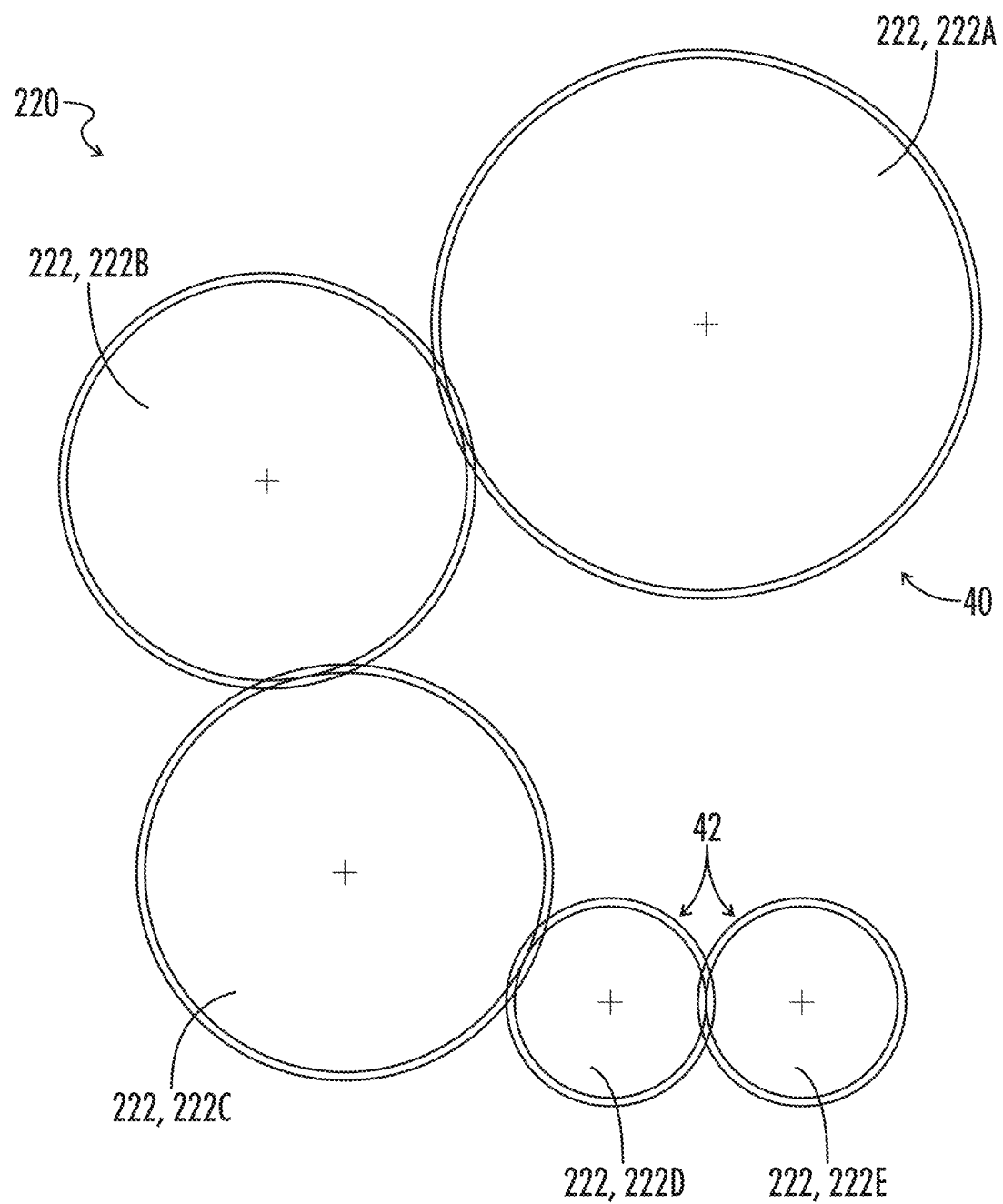
FIG. 1E is a view of a gearing system of the drive section of the embodiment of the bone grinder.

The drive mechanism 212 may include a gearing system 220 having one or more gears 222, as depicted in FIG. 1E. The one or more gears 222 of the gearing system 220 may operatively engage the one or more cutting elements, including the primary cutting element 40 and/or the secondary cutting element 42, and rotate the one or more cutting elements. The drive mechanism 212 may operatively engage the one or more drive shafts 216 through the gearing system 220; each of the one or more drive shafts 216 may engage at least one of the one or more cutting elements, including the primary cutting element 40 and/or the secondary cutting element 42. The drive mechanism 212, by and through the one or more gears 222 of the gearing system 220 and one or more clutches (not shown) may rotate the one or more cutting elements, including the primary cutting element 40 and/or the secondary cutting element 42. In optional embodiments, a piston-style rotary actuator (not shown) is the rotation force within the drive mechanism 212.

Referring to FIGS. 1A-1C, the processing section 24 of the bone grinder 20 may be attached to a wall 200 by a wall plate 202. The wall plate 202 may include wall-plate mounting studs 203, such as the wall-plate mounting studs 203A and 203B as depicted in FIGS. 1A and 1C, with which the processing section 24 of the bone grinder 20 may be attached to the wall 200. In optional embodiments, the wall plate 202 may also include proximity switches (not shown) that are configured to provide safety features for the bone grinder 20. To the extent any of the optional embodiments of the proximity switches (not shown) are not in connection, the bone grinder 20 will not operate. The proximity switches may be located near a connection of the chute 32 and/or near a connection of the one or more drive shafts 216 and the one or more cutting elements, including either the primary cutting element 40 and/or the secondary cutting element 42. As illustratively conveyed in FIGS. 1A-1C, the processing section 24 of the bone grinder 20 may have a front plate 204 mounted and/or affixed, such that the grinding chamber 30, the chute 32, and the discharge path 34 may be sealed or otherwise covered from external conditions, including contaminants, air, moisture, or other environmental factors.

The processing section 24 of the bone grinder 20 may be environmentally separated from the drive section 22 to deter, prevent, or mitigate a contamination of the processing section 22 with external conditions, including air, moisture, contaminants, or other environmental factors. The drive section 22 may be environmentally separated from the processing section 24 through mounting, fixing, and/or stabilizing the one or more drive shafts 216 onto a drive plate 214, thereby shielding and or further separating the one or more drive shafts 216 from the drive mechanism 212 and the control box 210. The drive section 22 may be further environmentally separated from the processing section 24 by mounting the processing section 24 on the wall 200 with the wall plate 202. And, the processing section 24 may be even further environmentally separated from the drive section 22 by mounting or affixing the front plate 24 so as to seal or cover the grinding chamber 30, the chute 32, and the discharge path 34. In optional embodiments, the processing section 24 of the bone grinder 20 may have a compressed air filtration system (not shown). The compressed air filtration system (not shown) may operate between about 60 pounds per square inch (psi) to about 160 pounds per square inch (psi). The compressed air filtration system (not shown) may remove impurities within the processing section 24 having dimensions at or around 0.1 microns.

Referring to FIG. 1D, the front plate 204 is removed, thereby conveying the grinding chamber 30, the chute 32, and the discharge path 34 of the processing section 24. The chute 32 may be configured to contain and direct the bone 10 into the grinding chamber 30. The chute 32, which is positioned before the grinding chamber 30, may contain a bone supplying cylinder 70, as illustratively conveyed in FIGS. 1A-1D. The bone supplying cylinder 70 may engage the grinding chamber 30, and the bone supplying cylinder 70 may be adapted to transport the bone 22 to the primary cutting element 40 within the grinding chamber 30. The bone supplying cylinder 70 within the chute 32 may include a bone supplying rod 72 having a contact plate 74. In optional embodiments, the bone supplying cylinder 70 may be formed of a material including at least one of low carbon, non-magnetic, stainless steel, or other metals, metallic alloys, polymeric materials, or combinations thereof.

In optional embodiments, the bone supplying rod 72 of the bone supplying cylinder 70 may be pneumatically driven, so as to deliver the bone 10 at a consistent pressure and speed to the grinding chamber 30. The use of a pneumatically-driven bone supplying rod 72 of the bone supplying cylinder 70 may transport the bone 10 to the primary cutting element 40 within the grinding chamber 30. Generally, the use of the pneumatically-driven bone supplying rod 72 may necessitate a high degree of torque, including over about 71,000 inches per pound, so as to apply consistent pressure to the bone 10 as it is transported to the grinding chamber 30. In other optional embodiments, the bone supplying rod 72 of the bone supplying cylinder 70 may utilize or incorporate a hydraulic cylinder, a turbine piston, or other devices within the industry for delivering consistent power, pressure, and/or speed. In further optional embodiments, the bone supplying rod 72 of the bone supplying cylinder 70 may be electro-mechanically driven, enabling a user of the bone grinder 20 to control, regulate, or otherwise monitor the pressure and speed applied to the bone 10 by the bone supplying rod 72 as the bone 10 is transported to the primary cutting element 40 within the grinding chamber 30. By using an electro-mechanically driven bone supplying cylinder 70, the bone grinder 20 may not require or necessitate any pneumatic lines plumbed or connected to the processing section 24, eliminating a risk of inadvertent leaks or undue contamination of the grinding chamber 30.

The bone supplying cylinder 70 may be opened at or near the chute 32 to enable a loading or entry of the bone 10 into the chute 32 and then the grinding chamber 30. The bone supplying cylinder 70 may be attached to the chute 32 by one or more dowel pins 76, including a first dowel pin 76A and second dowel pin 76B, as depicted in FIGS. 1A-1C. In optional embodiments, the user of the bone grinder 20 may remove the one or more dowel pins 76, tilt the bone supplying cylinder 70, and load or place the bone 10 at or near the chute 32 for processing. In further optional embodiments, where the bone supplying cylinder 70 is titled, the bone supplying cylinder 70 may rest on a stop, a pin, or a wedge (not shown). The bone supplying cylinder 70 and the chute 32 may have a diameter of 1.5 inches. In other embodiments, the bone supplying cylinder 70 and the chute 32 may have a diameter ranging from about one (1) inch to about two (2) inches, though can be higher or lower. The diameter of the bone supplying cylinder 70 and the chute 32 must be adequate to receive the bone 10, whether the bone 10 has cortical and/or cancellous bone mass. In yet further optional embodiments, the bone supplying cylinder 70 and the chute 32 may receive up to around ten (10) inches of the bone 10, and in other embodiments, the bone supplying cylinder 70 and the chute 32 may receive a length of the bone 10 that is greater than or lesser than ten (10) inches.

Within the bone supplying cylinder 70 may be the bone supplying rod 72 and the contact plate 74 at an end of the bone supplying rod 72. Generally, the bone supplying rod 72, when entering the bone supplying cylinder 70 and the chute 32, is not configured to rotate. The contact plate 74 of the bone supplying rod 72 may engage the bone 10 upon loading the bone 10 into the bone supplying cylinder 70 and the chute 32. The contact plate 74, by and through the bone supplying rod 72, may transport the bone 10 to the primary cutting element 40 within the grinding chamber 30. In optional embodiments, the contact plate 74 may have a curvature with a circumference 75 similar or complementary to a circumference associated with a diameter 80 or a diameter 90 of the primary cutting element 40. This correlation may permit the bone 20 to reach the primary cutting element 40 within the grinding chamber 30 as the contact plate 74 of the bone supplying rod 72 transports the bone 10 to the primary cutting element 40 within the grinding chamber 30. In other optional embodiments, the contact plate 74 may comprise a four-sided end, such as a square, rectangle, or other four-sided polygon; in yet further optional embodiments, where the contact plate 74 comprises the four-sided end, the contact plate may have dimensions of about 1.5 inches by about 2 inches, though in other embodiments the dimensions can be higher or lower.

Referring to FIG. 1D, the bone supplying rod 72 of the bone supplying cylinder 70 may be configured to direct the bone 10 into the chute 32 and further to the primary cutting element 40 within the grinding chamber 30. As illustratively conveyed in FIG. 1D, the primary cutting element 40 include the coarse cutting tool 50 and the secondary cutting element 42 may include one or more of the fine cutting tool 52. The primary cutting element 40 and the secondary cutting element 42 may be operable to grind, shear, slice, or otherwise cut the bone 10 into the bone matter 12. In optional embodiments, the primary cutting element 40 may be operable to grind, shear, slice, or otherwise cut the bone 10 in the bone matter 12, whereby the bone matter 12 constitutes intermediary pieces, such as the bone fragments 14. In other optional embodiments, the primary cutting element 40 may be operable to grind, shear, slice, or otherwise cut the bone 10 in the bone matter 12, whereby the bone matter 12 constitutes particulate pieces, such as the bone powder 16. In yet further optional embodiments, the secondary cutting element 42 may be operable to grind, shear, slice, or otherwise cut the bone 10 into the bone matter 12, whereby the bone matter 12 constitutes particulate pieces, such as the bone powder 16. Where the bone matter 12 may constitute intermediary pieces, such as the bone fragments 14, a size of the intermediary pieces may generally range from about 1,000 microns to about 6,000 microns, though in other embodiments the size of the intermediary pieces can be higher or lower. Where the bone matter 12 may constitute particulate pieces, such as the bone powder 16, a size of the particulate pieces may generally range from about 125 microns to about 2,000 microns, though in other embodiments the size of the particulate pieces can be higher or lower. A size of the intermediary pieces, such as the bone fragments 14, or a size of the particulate pieces, such as the bone powder 16, are determined by cutting teeth of the primary cutting element 40 and/or the secondary cutting element 42, including shape, height, spacing, angle, polish, and depth of alternating recesses and ridges of the cutting teeth of the primary cutting element 40 and/or the secondary cutting element 42.

Referring to FIG. 1D, the front plate 204 is removed, thereby conveying the chute 32, the grinding chamber 30, and the discharge path 34 of the processing section 24. The grinding chamber 30 may have an intermediate zone 36 separating the primary cutting element 40 from the secondary cutting element 42. The intermediate zone 36 may have a first wall 37 and a second wall 38, wherein a distance 39 between the first wall 37 and the second wall 38 generally decreases from the primary cutting element 40 to the secondary cutting element 42. In optional embodiments, the first wall 37 and the second wall 38 may slope inward in a generally linear manner. In other optional embodiments, the first wall 37 and the second wall 38 may slope inward in a generally curved manner. In further optional embodiments, the intermediate zone 36 may occupy a volume within the grinding chamber 30 that is about 12 in$^3$. In other embodiments, the intermediate zone 36 may occupy a volume within the grinding chamber 30 that is at least between about 2.5 in$^3$ and about 13 in$^3$, though in other embodiments the intermediate zone 36 may occupy a volume within the grinding chamber 30 that is greater than or lesser than the aforementioned values.

In yet further optional embodiments, the primary cutting element 40 may have a primary first end 44 opposed to a primary second end 45, such that the primary first end 44 is adjacent to the chute 32 and the primary second end 45 is adjacent to the intermediate zone 36. The secondary cutting element 42 may have a secondary first end 46 opposed to a secondary second end 47, such that the secondary first end 46 is adjacent to the intermediate zone 36 and the secondary second end 47 is adjacent to the discharge path 34. The primary second end 45 of the primary cutting element 40 may be a distance 48 from the secondary first end 46 of the secondary cutting element 42 that is about 2.85 inches. In other embodiments, the distance 48 may range from about 0.75 inches to about 3 inches, though in optional embodiments the distance 48 can be higher or lower. The intermediate zone 36 of the present disclosure may deter, mitigate, or prevent a "bone swirling" effect, whereby the bone matter 12, as the bone matter 12 transfers from the primary cutting element 40 to the secondary cutting element 42, either does not transfer to the secondary cutting element 42, and further to the discharge path 34, or the bone matter 12 moves in a "swirling" motion in the intermediate zone 36 between the primary cutting element 40 and the secondary cutting element 42. By having the bone matter 12 "swirl" in the intermediate zone 36 or not transfer to the secondary cutting element 42, the bone grinder 20 is prevented or delayed from efficiently transforming or converting the bone 10 into the bone matter 12. And, where the bone grinder 20 is delayed from efficiently transforming or converting the bone 10 into the bone matter 12, unnecessary heat may be generated or dissipated in the grinding chamber 30, the heat of which degrades, diminishes, decreases, or breaks down the osteoinductivity of the bone 10.

Referring to FIGS. 1A-1D, the primary cutting element 40 and the secondary cutting element 42, which are positioned within the grinding chamber 30, may sequentially perform the primary cutting operations and the secondary cutting operations on the bone 10 to produce the bone matter 12. The drive mechanism 212 may operatively engage the primary cutting element 40 and the secondary cutting element 42 to perform the primary cutting operations and the secondary cutting operations.

Referring to FIGS. 2A-2B, an embodiment of the coarse cutting tool 50 is depicted. In optional embodiments, the primary cutting element 40 may be the coarse cutting tool 50, as illustratively conveyed in FIGS. 1A-1D. The coarse cutting tool 50 may have the diameter 80 ranging from about 2.9 inches to about 3 inches, though in other embodiments the diameter 80 can be higher or lower. Moreover, the coarse cutting tool 50 may have an axial length 82 ranging from about 1.9 inches to about 2 inches, though in other embodiments the diameter 80 can be higher or lower. The coarse cutting tool 50, which may be referred to as a primary cutting tool 50 of the primary cutting element 40, may have coarse cutting teeth 84, which may be referred to as primary cutting teeth 84. The coarse cutting teeth 84 may have one or more rows of alternating ridges 88 and recesses 86. In optional embodiments, each of the one or more rows of the alternating ridges 88 and recesses 86 may be offset and vary in starting location along the axial length 82. In other optional embodiments, each of the ridges 88 of the coarse cutting teeth 84 may have a ridge width 89 ranging from about 0.030 inches to about 0.25 inches, though in other embodiments the ridge width 89 can be higher or lower. In further optional embodiments, each of the recesses 86 of the coarse cutting teeth 84 may have a recess width 87 ranging from about 0.1 inches to about 0.55 inches, though in other embodiments the recess width 87 can be higher or lower. As previously stated, the coarse coating tool 50 may be operable to grind, shear, slice, or otherwise cut the bone 10 into bone matter 12, such as the bone fragments 14, wherein the bone fragments 14 may range in size from about 1,000 microns to about 6,000 microns, though in other embodiments the size of the bone fragments 14 can be higher or lower.

Figure 3A:
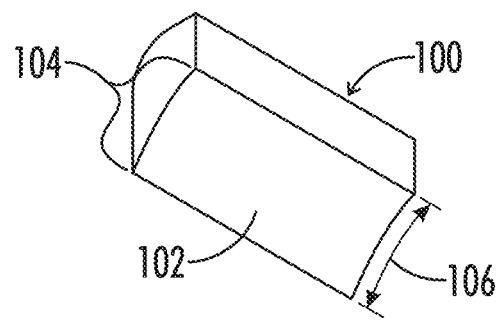
FIG. 3A is a perspective view of a scraper to be positioned within a grinding chamber of an embodiment of a bone grinder.
Figure 3B:
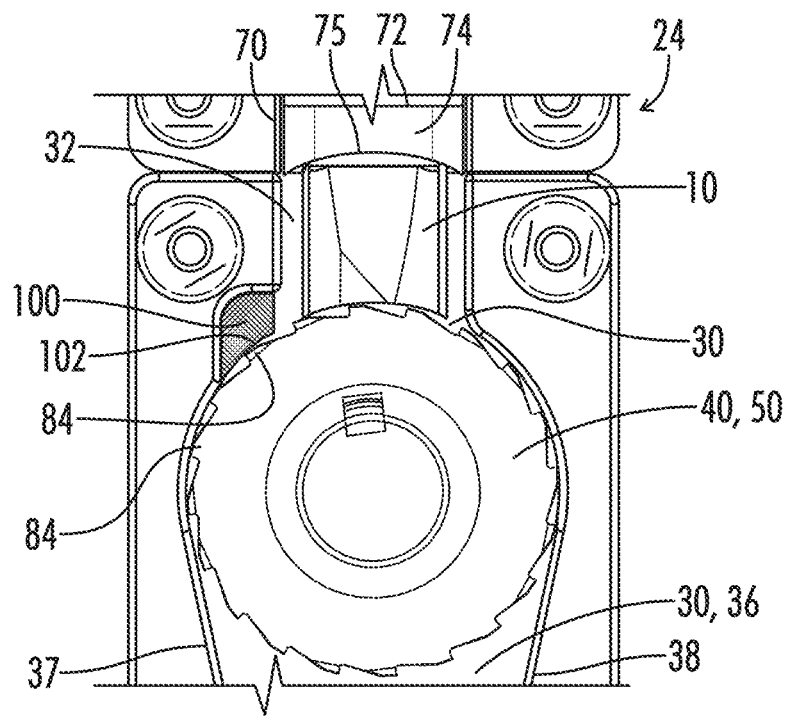
FIG. 3B is a front view of the embodiment of the bone grinder having the scraper positioned within the grinding chamber and proximate to a coarse cutting tool.
Figure 4A:
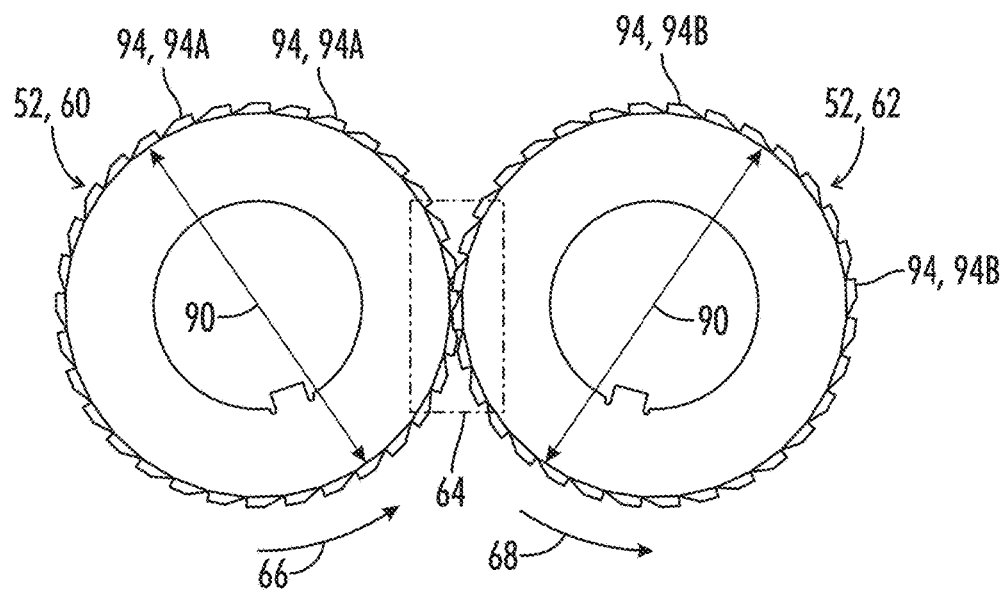
FIG. 4A is a front view of fine cutting tools to be positioned within a grinding chamber of an embodiment of a bone grinder.
Figure 4B:
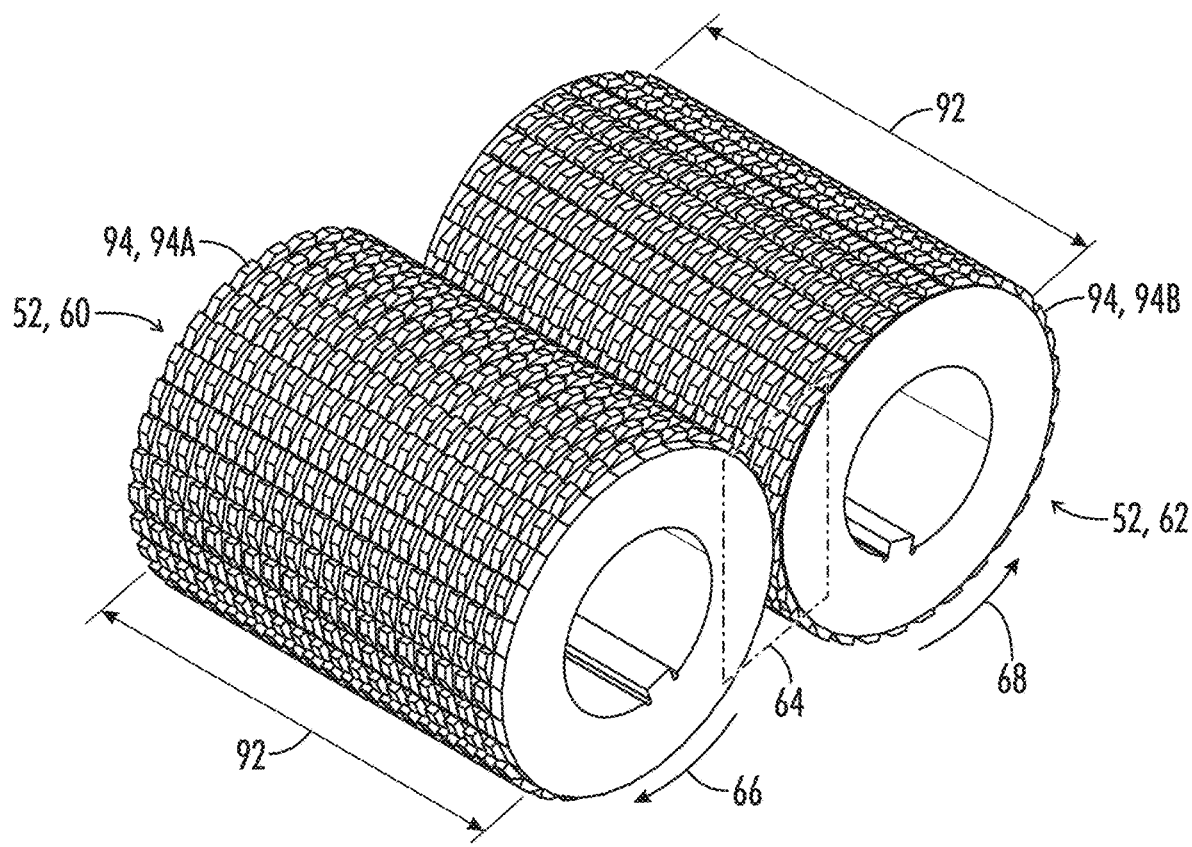
FIG. 4B is a perspective view of the fine cutting tools to be positioned within the grinding chamber of the embodiment of the bone grinder.
Figure 4C:
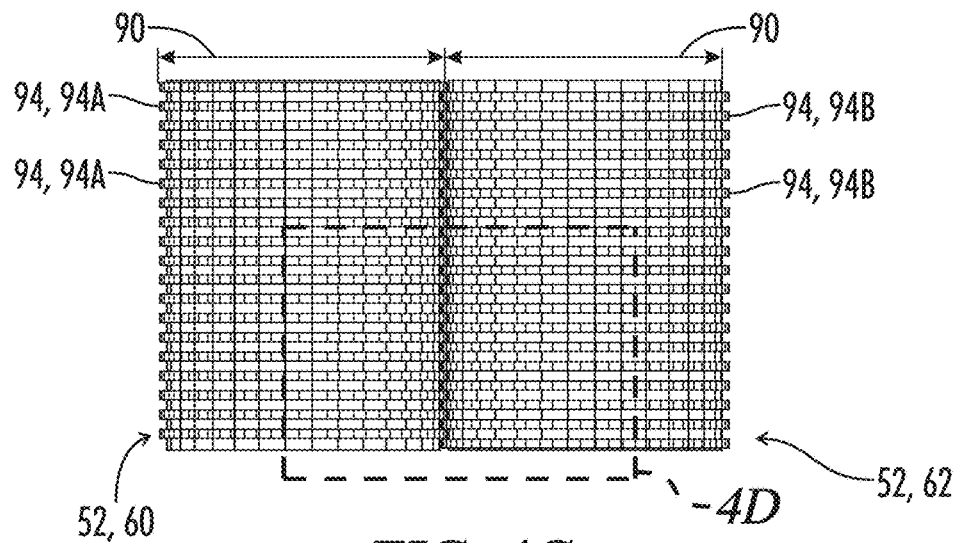
FIG. 4C is a top view of the fine cutting tools to be positioned within the grinding chamber of the embodiment of the bone grinder.
Figure 4D:
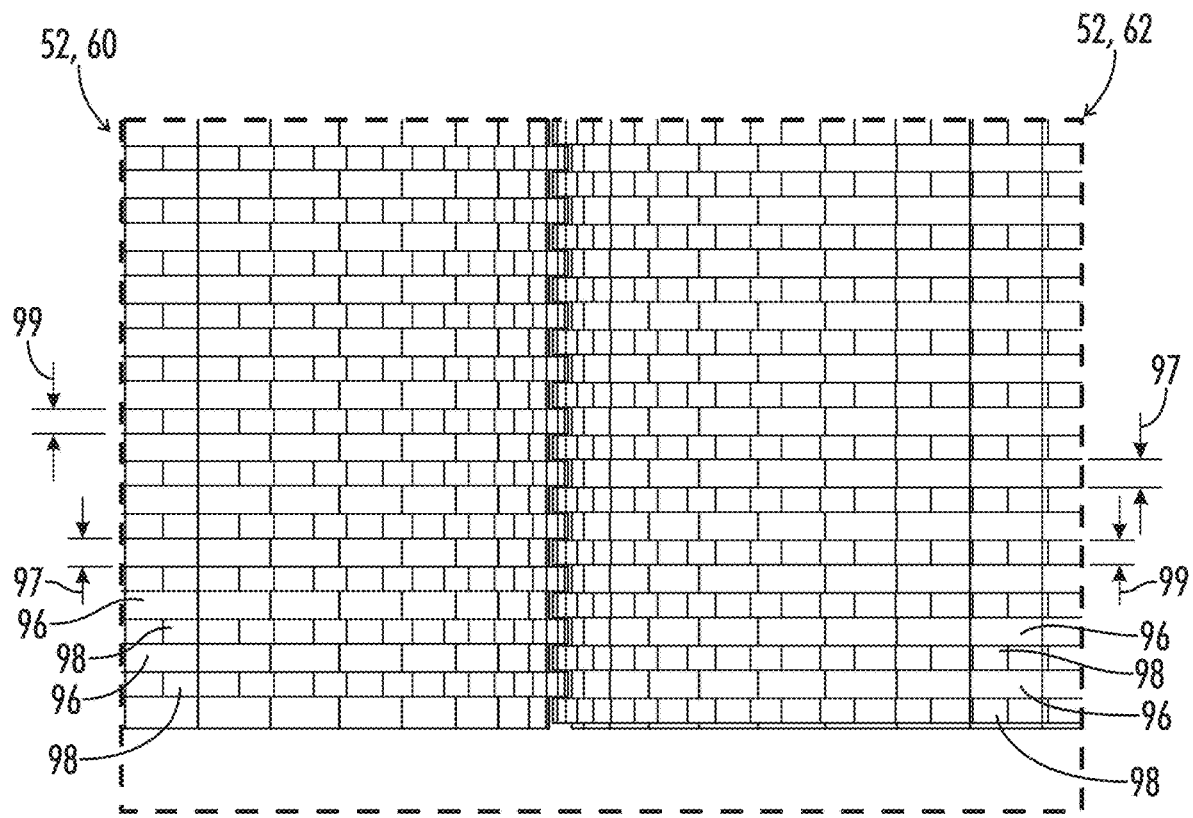
FIG. 4D is an enhanced top view of the fine cutting tools to be positioned within the grinding chamber of the embodiment of the bone grinder.

Referring to FIGS. 3A-3B, various embodiments of a scraper 100 are depicted. The scraper 100 may have a scraping edge 102. The scraper 100 may be located within the grinding chamber 30 and proximate to or in contact with the primary cutting element 40, which, in optional embodiments, may be the coarse cutting tool 50. In optional embodiments, the scraping edge 102 of the scraper 100 may have a curvature with a circumference 106 similar or complementary to a circumference associated with the diameter 80 of the primary cutting element 40. This correlation may permit the primary cutting element 40 within the grinding chamber 30 to continue to rotate without obstruction, thereby grinding, shearing, slicing, or otherwise cutting the bone 10. The scraping edge 102 of the scraper 100 may be configured to scrape the bone matter 12, such as the bone fragments 14, from the primary cutting element 40. By scraping the bone matter 12, such as the bone fragments 14, from the primary cutting element 40, the milling operation of the bone grinder 20 is not interrupted, enabling the bone grinder 20 to operate more efficiently or as an automated process. By operating without interruption, unnecessary heat is not generated or dissipated, the heat of which diminishes or breaks down the osteoinductivity of the bone 10. In optional embodiments, the scraping edge 102 may have a surface area 104 ranging from about 0.4 in$^2$ to about 2.5 in$^2$, though in other embodiments the surface area 104 can be higher or lower.

Referring to FIGS. 4A-4D, an embodiment of the fine cutting tool 52 is depicted. In optional embodiments, the secondary cutting element 42 may be the fine cutting tool 52, as illustratively conveyed in FIGS. 4A-4D. The secondary cutting element 42 may include a first cutting tool 60 and a second cutting tool 62. Where the fine cutting tool 52 functions or operates as the secondary cutting element 42, the first cutting tool 60 may be referred to as a first secondary cutting tool 60 and the second cutting tool 62 may be referred to as the second secondary cutting tool 62. The embodiment of the fine cutting tool 52, as illustratively conveyed in FIGS. 4A-4D, is not intended to limit the fine cutting tool 52 to function or operate as the secondary cutting element 42. In other embodiments of the bone grinder 20, the fine cutting tool 52 may function or operate as the primary cutting element 40. Where the fine cutting tool 52 functions or operates as the primary cutting element 40, the first cutting tool 60 may be referred to as a first primary cutting tool 60 and the second cutting tool 62 may be referred to a second primary cutting tool 62.

Referring to FIGS. 4A-4D, the first cutting tool 60 may have a first set of fine cutting teeth 94A and the second cutting tool 62 may have a second set of fine cutting teeth 94B. For the purpose of the disclosure, the first set of fine cutting teeth 94A and the second set of fine cutting teeth 94B may be referred as to as fine cutting teeth 94. The first cutting tool 60 and the second cutting tool 62 may be positioned to define a cutting zone 64 between the first set of fine cutting teeth 94A and the second set of fine cutting teeth 94B. The first set of fine cutting teeth 94A may be positioned within the cutting zone 64 to alternate with and overlap with the second set of fine cutting teeth 94B. In optional embodiments, the first set of fine cutting teeth 94A may move in a first direction 66 through the cutting zone 64 and the second set of fine cutting teeth 94B may move in a second direction 68 through the cutting zone 64. The first direction 66 and the second direction 68 may be similar, such that the first direction 66 and the second direction 68 are both clockwise or counterclockwise. In other optional embodiments, the first direction 66 and the second direction 68 may be different, such that the first direction 66 is clockwise and the second direction 68 is counterclockwise (or vice versa).

Referring to FIGS. 4A-4D, the fine cutting tool 52 may have the diameter 90 ranging from about 1.4 inches to about 1.5 inches, though in other embodiments the diameter 90 can be higher or lower. Moreover, the fine cutting tool 52 may have an axial length 92 ranging from about 1.9 inches to about 2 inches. The fine cutting tool 52 may have the fine cutting teeth 94. The fine cutting teeth 94 may have one or more rows of alternating ridges 98 and recesses 96. In optional embodiments, each of the one or more rows of alternating ridges 98 and recesses 96 may be offset and vary in starting location along the axial length 92. In other optional embodiments, each of the ridges 98 of the fine cutting teeth 94 may have a ridge width 99 ranging from about 0.01 inches to about 0.1 inches, though in other embodiments the ridge width 99 can be higher or lower. In further optional embodiments, each of the recesses 96 of the fine cutting teeth 94 may have a recess width 97 ranging from about 0.02 inches to about 0.15 inches, though in other embodiments the recess width 97 can be higher or lower. The first set of fine cutting teeth 94A may at least partially overlap and alternate with the second set of fine cutting teeth 94B, thereby facilitating an interaction between the first set of fine cutting teeth 94A and the second set of fine cutting teeth 94B to grind, shear, slice, or otherwise cut the bone 10. As previously stated, the fine cutting tool 52 may be operable to grind, shear, slice, or otherwise cut the bone 10 into bone matter 12, such as the bone powder 16, wherein the bone powder 16 may range in size from about 125 microns to about 2,000 microns, though in other embodiments the size of the bone powder 16 can be higher or lower.

Figure 5A:
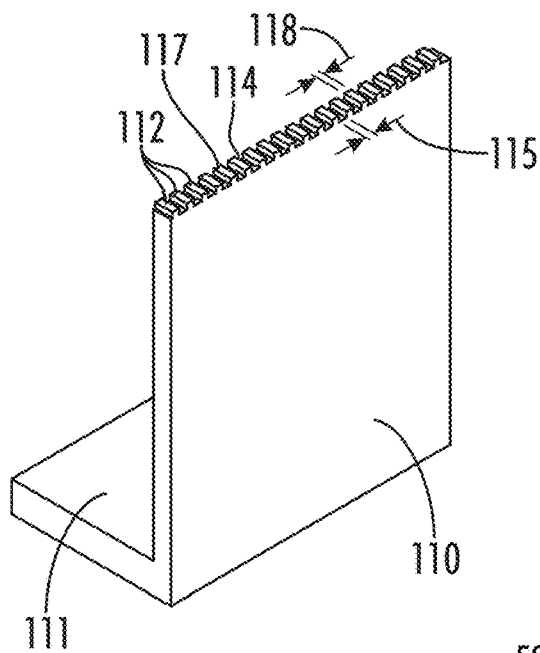
FIG. 5A is a perspective view of a rake to be positioned within a grinding chamber of an embodiment of a bone grinder.
Figure 5B:
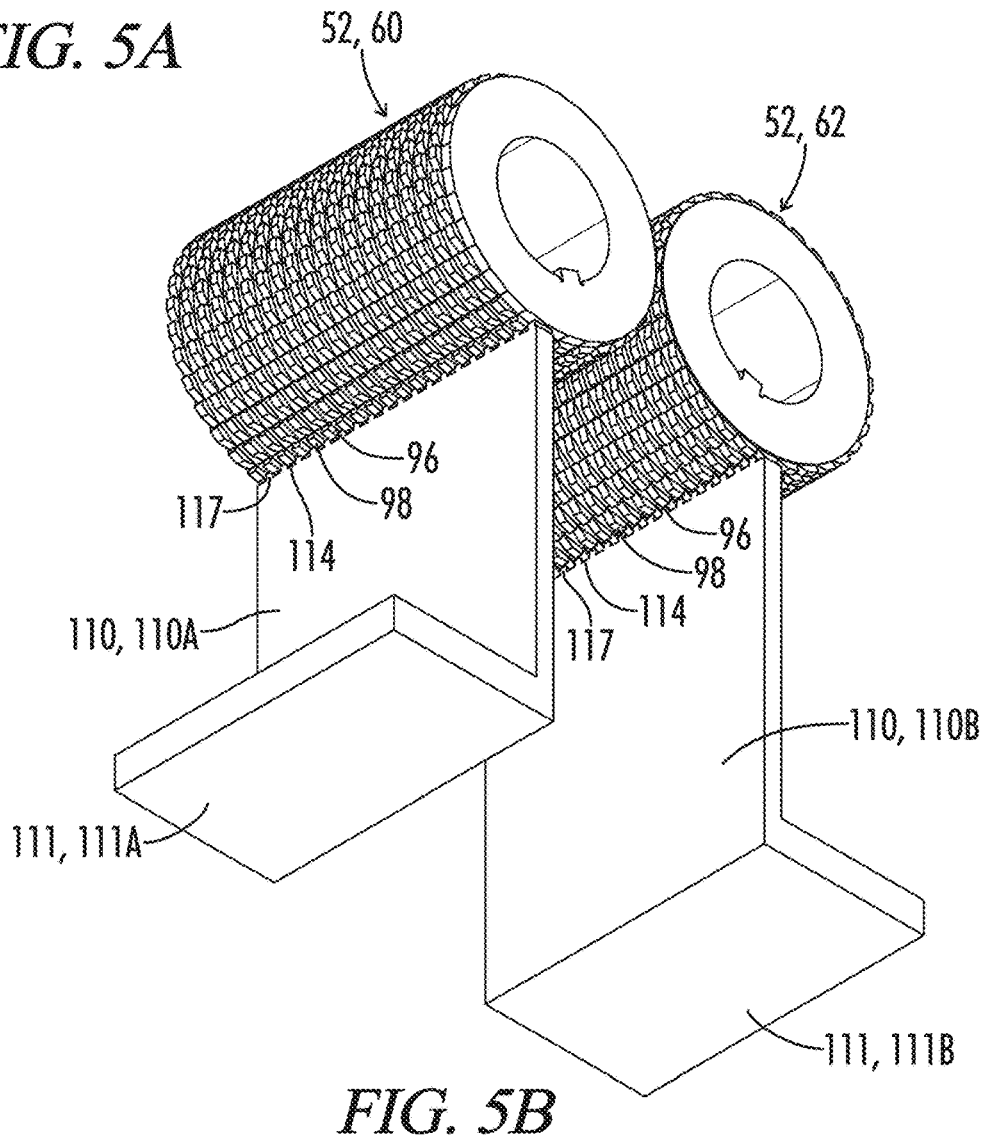
FIG. 5B is a perspective view of the rake engaged to each of fine cutting tools to be positioned within the grinding chamber of the bone grinder.
Figure 5C:
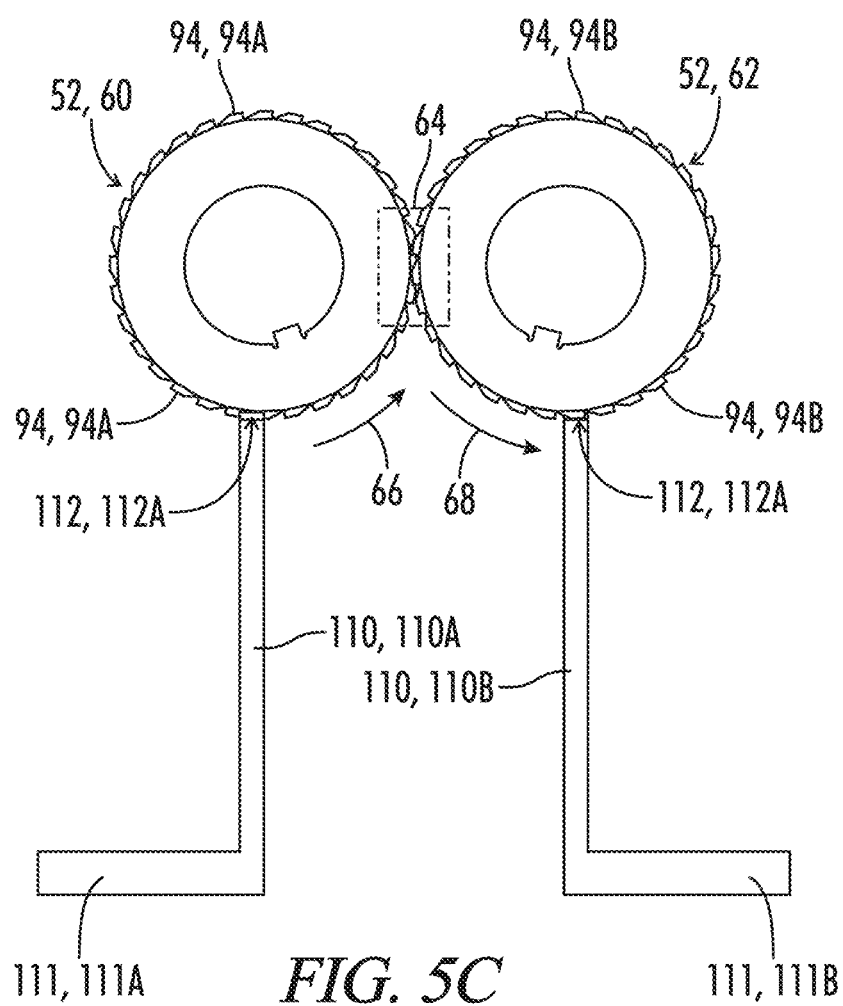
FIG. 5C is a front view of the rake engaged to each of the fine cutting tools to be positioned within the grinding chamber of the bone grinder.
Figure 5D:
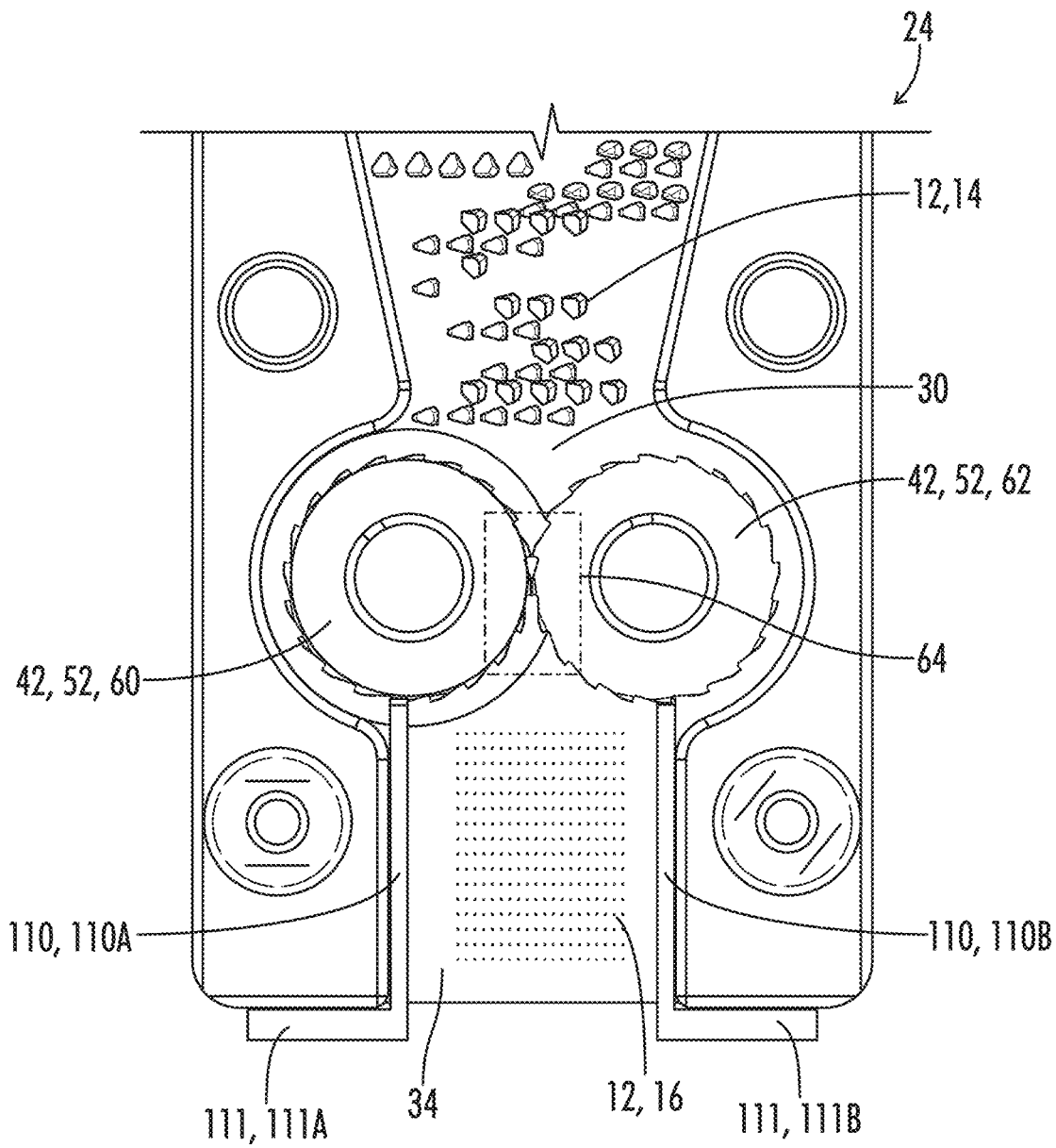
FIG. 5D is a front view of an embodiment of the bone grinder having the rake positioned within the grinding chamber and engaged to each of the fine cutting tools.

Referring to FIGS. 5A-5C, various embodiments of a rake 110 are depicted. The rake 110 may include raking teeth 112. The raking teeth 112 may have a row of alternating ridges 117 and recesses 114. In other optional embodiments, each of the ridges 117 of the raking teeth 112 may have a ridge width 118 ranging from about 0.01 inches to about 0.1 inches, though in other embodiments the ridge width 118 can be higher or lower. In further optional embodiments, each of the recesses 114 of the raking teeth 112 may have a recess width 115 ranging from about from about 0.02 inches to about 0.15 inches, though in other embodiments the recess width 115 can be higher or lower. The rake 110 may be positioned within the grinding chamber 30 and after the primary cutting element 40, where the primary cutting element 40 includes the fine cutting tool 52, or the rake 110 may be positioned within the grinding chamber 30 after the secondary cutting element 42, where the secondary cutting element 42 includes the fine cutting tool 52. In optional embodiments, the rake 110 may be positioned within the grinding chamber 30 after the secondary cutting element 42, such that a perpendicular support member 111 may engage the raking teeth to the fine cutting tool 52. The perpendicular support member 111 may be mounted at a location adjacent to the discharge path 34, whereby the perpendicular support member 111 does not obstruct or interfere with a movement of the milled bone matter 12, whether as the bone fragments 14 or the bone powder 16. The raking teeth 112 of the rake 110 may be engaged to the fine cutting teeth 94 of the fine cutting tool 52. The row of alternating ridges 117 and recesses 114 of the raking teeth 112 may correspond with the row of alternating ridges 98 and recesses 96 of the fine cutting teeth 94. In optional embodiments, a first set of raking teeth 112A of a first rake 110A may be engaged to the first set of fine cutting teeth 94A and a second set of raking teeth 112B of a second rake 110B may be engaged to second set of fine cutting teeth 94B. The first rake 110A may associate with a first perpendicular support member 111A, and the second rake 110B may associate with a second perpendicular support member 111B. The engagement and correspondence of the raking teeth 112 to the fine cutting teeth 94 may discharge or remove "stuck," "lodged," or "adhered" bone matter 12 in the fine cutting teeth 94, whether as the bone fragments 14 or the bone powder 16. By raking the bone matter 12, such as the bone fragments 14 and/or the bone powder 16, from the primary cutting element 40 or the secondary cutting element 42, the milling operation of the bone grinder 20 is not interrupted, enabling the bone grinder 20 to operate more efficiently or as an automated process. By operating without interruption, unnecessary heat is not generated or dissipated, the heat of which diminishes or breaks down the osteoinductivity of the bone 10.

Referring to FIGS. 1A-1D, once the bone 10 has been grinded, sheared, sliced, or otherwise cut by the primary cutting element 40 and/or the secondary cutting element 42, such that the bone 10 has been converted or transformed into bone matter 12, including the bone fragments 14 or the bone powder 16, the bone matter 12 may exit the grinding chamber 30 and the bone grinder 20 through the discharge path 34. The discharge path 34 may be positioned after the grinding chamber 30, and the discharge path 34 may be distally located from the bone supplying cylinder 70 and the chute 32.

Referring to FIG. 1E, the drive mechanism 212 may include the gearing system 220. The gearing system 220 may operatively engage the primary cutting element 40 and/or the secondary cutting element 42, thereby rotating the primary cutting element 40 and/or the secondary cutting element 42. The drive mechanism 212 operatively engages the one or more drive shafts 216, with each of the one or more drive shafts operatively engaging at least one of the primary cutting element 40 and/or the secondary cutting element 42. The gearing system 220 may comprise the one or more gears 222, including a first gear 222A corresponding to the primary cutting element 40, a second gear 222B, a third gear 222C, and a fourth gear 222D and a fifth gear 222E corresponding to the secondary cutting element 42. For the purpose of the disclosure herein, the first gear 222A, the second gear 222B, the third gear 222C, the fourth gear 222D, and the fifth gear 222E may be referred to as the one or more gears 222.

Figure 6A:
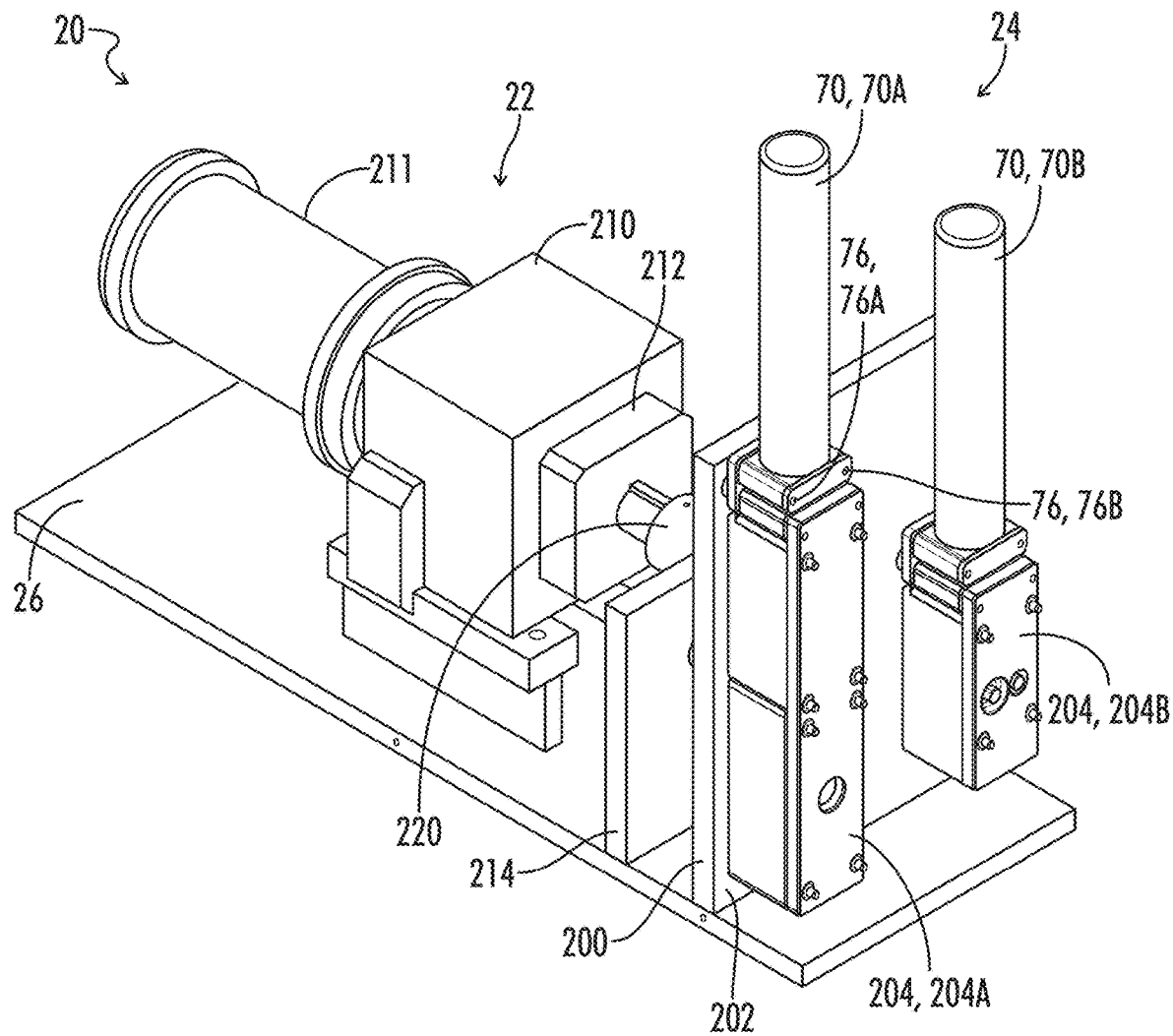
FIG. 6A is a perspective view of an alternative embodiment of a bone grinder having a drive section and a processing section.
Figure 6B:
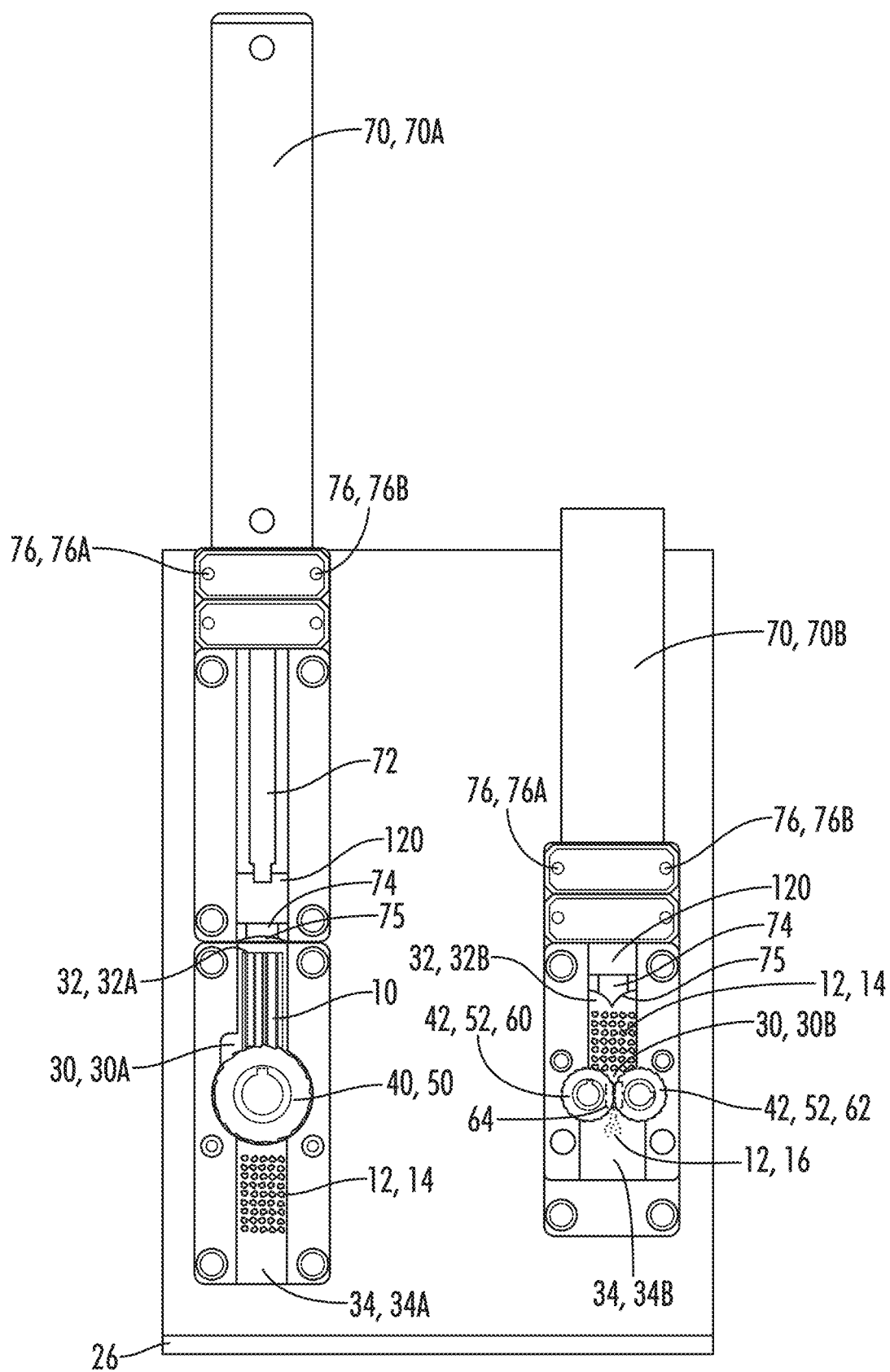
FIG. 6B is a front view of the alternative embodiment of the bone grinder with a front plate removed conveying a first chute and a second chute, a first grinding chamber and a second grinding chamber, and a first discharge path and a second discharge path of the processing section.

Referring to FIGS. 6A-6B, an alternative embodiment of the bone grinder 20 is depicted. For the purpose of the disclosure herein, the alternative embodiment of the bone grinder 20 may be described by, comprise, or otherwise include features, elements, or objects described in connection with the embodiment of the bone grinder 20 depicted in FIGS. 1A-1D. Referring to FIG. 6A, the processing section 24 of the bone grinder 20 may have a first front plate 204A and a second front plate 204B sealing or covering the grinding chamber 30, the chute 32, and the discharge path 34. Referring to FIG. 6B, the processing section 24 of the bone grinder 20 may include a first grinding chamber 30A and a second grinding chamber 30A, a first chute 32A and a second chute 32B, and a first discharge path 34A and a second discharge path 34B. The first chute 32A may correspond to a first bone supplying cylinder 70A and the second chute 32B may correspond to a second bone supplying cylinder 70B. In the alternative embodiment of the bone grinder 20, the user of the bone grinder 20 may insert, load, or otherwise place the bone 10 into either (or both) of the first bone supplying cylinder 70A and the second bone supplying cylinder 70B. The first grinding chamber 30A may include the coarse cutting tool 50, which may constitute the primary cutting element 40 performing the primary cutting operation on the bone 10. The second grinding chamber 30B may include the fine cutting tool 52, which may constitute the primary cutting element 40 performing the primary cutting operation on the bone 10 or the secondary cutting element 42 performing the secondary cutting operation on the bone 10. In optional embodiments, the user may place the bone 10 into the first grinding chamber 30A, thereby grinding, shearing, slicing, or cutting the bone 10 into the bone matter 12, such as the bone fragments 14, which exits the first discharge path 34A. Thereafter, the user may take the bone matter 12, such as the bone fragment 14, and insert the bone fragments 14 into the second grinding chamber 30B, thereby grinding, shearing, slicing, or cutting the bone fragments 14 into the bone powder 16 with the secondary cutting element 42 of the second grinding chamber 30B.

For the purpose of the disclosure, when referring to the front plate 204, the front plate 204 may constitute either (or both) the first front plate 204A or the second front plate 204B; when referring to the grinding chamber 30, the grinding chamber 30 may constitute either (or both) the first grinding chamber 30A or the second grinding chamber 30B; when referring to the chute 32, the chute 32 may constitute either (or both) the first chute 32A or the second chute 32B; when referring to the discharge path 34, the discharge path 34 may constitute either (or both) the first discharge path 34A or the second discharge path 34B; and, when referring to the bone supplying cylinder 70, the bone supplying cylinder 70 may constitute either (or both) the first bone supplying cylinder 70A or the second bone supplying cylinder 70B.

As shown in FIGS. 6A-6B, the bone grinder 20 may have a push platform 120 placed or incorporated within the chute 32. The push platform 120 may be operable between a compressed position and a released position. In the compressed position, the push platform 120 may be configured to enable the drive mechanism 212 to operatively engage the primary cutting element 40 and/or the secondary cutting element 42 where the chute 32 contains the bone 10 to the transported or guided to the grinding chamber 30. In the released position, the push platform 120 may be configured to operatively disengage the primary cutting element 40 and/or the secondary cutting element 42 from performing primary cutting operations and or secondary cutting operations for when the chute 32 does not contain the bone 10 to be transported or guided to the grinding chamber 30. In optional embodiments, the bone supplying rod 72 of the bone supplying cylinder 70 may direct the bone 10 into the chute 32 and the grinding chamber 30, such that the push platform 120 may be operated to the compressed position. In other optional embodiments, where the bone supplying rod 72 of the bone supplying cylinder 70 does not transport or guide the bone 10 into the grinding chamber 30 and the bone supplying rod 72 is at least partially withdrawn from the chute 32, the push platform 120 may be operated to the released position. Where the push platform 120 is operated to the released position, unnecessary heat is not generated or dissipated through the milling operation of the primary cutting element 40 and/or the secondary cutting element 42. In other words, the user need not conjecture, estimate, or guess when the bone 10 is adequately grinded, sheared, sliced, or cut, such that the bone 10 is converted or transformed into the bone matter 12, including the bone fragments 14 or the bone powder 16. Thus, the push platform 120 may deter, mitigate, or prevent an unnecessary generation or dissipation of heat in the grinding chamber 30, thereby preserving or promoting the osteoinductivity of the bone 10 or the bone matter 12, whether as the bone fragments 14 or the bone powder 16.

Figure 6C:
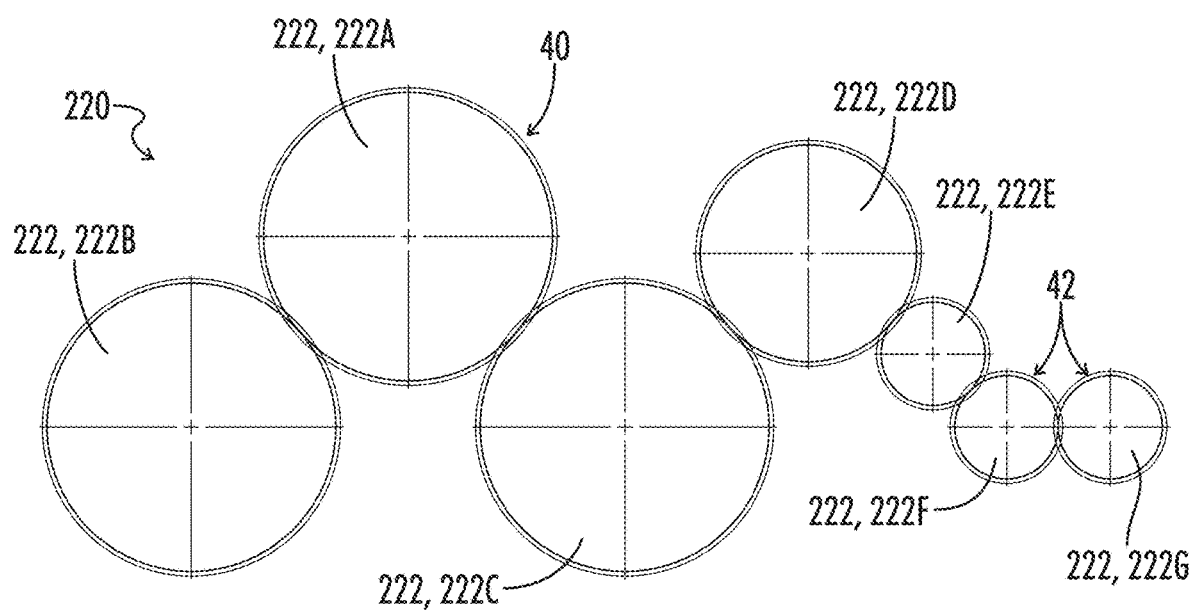
FIG. 6C is a view of a gearing system of the drive section of the alternative embodiment of the bone grinder.

In optional embodiments of the bone grinder 20 illustratively conveyed in FIGS. 6A-6C, the push platform 120 may include a reed switch (not shown). The reed switch may be configured to operatively disengage the primary cutting element 40 and/or the secondary cutting element 42 from performing primary cutting operations and/or secondary cutting operations where the push platform 120 is operated to the released position. The reed switch may be operable between an open position corresponding to the released position and a closed position corresponding to the compressed position. When the push platform 120 is operated to the compressed position, the reed switch may be operated to the closed position such that an electric circuit is established, thereby permitting a flow of electric current to power the drive mechanism 212. When the push platform 120 is operated to the released position, the reed switch may be operated to the open position such that an electric circuit is not established, thereby preventing a flow of electric current to power the drive mechanism 212. Generally, for those embodiments of the bone grinder 20 having the reed switch in conjunction with the push platform 120, the drive mechanism 212 is driven by electric, electro-pneumatic, or electro-mechanical input.

Referring to FIGS. 6A-6C, a milling operation of the bone grinder 20 may proceed as follows. The bone 10 may be loaded or placed into the first bone supplying cylinder 70A and the first chute 32A for entry into the first grinding chamber 30A. Upon compressing the push platform 120 by inserting the bone supplying rod 72 and/or the bone 20, the push platform 120 may be operated to the compressed position, such that the drive mechanism 212 may operatively engage and cause to rotate the primary cutting element 40. Upon the primary cutting element 40 grinding, shearing, slicing, or cutting the bone 20 into the bone matter 12, such as the bone fragments 14, the primary cutting element 40 may continue to rotate so as to ensure the bone 20 is adequately grinded, sheared, sliced, or cut prior to terminating a rotation or milling of the primary cutting element 40. In optional embodiments, the control box 210 of the drive section 22 may include a programmable logic controller (PLC), configured to initiate a delay or pause sequence when the push platform 120 is operated to the compressed position, so as to ensure the bone 20 is adequately grinded, sheared, sliced, or cut prior to terminating a rotation or milling of the primary cutting element 40. Where the bone matter 12, such as the bone fragments 14, exits the first grinding chamber 30A through the first discharge path 34A, the user of the bone grinder 20 may transfer the bone matter 12 to the second bone supplying cylinder 70B and the second chute 32B for entry into the second grinding chamber 30B. Upon compressing the push platform 120 by inserting the bone supplying rod 72, the push platform 120 may be operated to the compressed position, such that the drive mechanism 212 may operatively engage and cause to rotate the secondary cutting element 42. Upon the secondary cutting element 42 grinding, shearing, slicing, or cutting the bone 20 into the bone matter 12, such as the bone powder 16, the secondary cutting element 42 may continue to rotate so as to ensure the bone 20 is further grinded, sheared, sliced, or cut prior to terminating a rotation or milling of the secondary cutting element 42. In optional embodiments, the control box 210 of the drive section 22 may include a programmable logic controller (PLC), configured to initiate a delay or pause sequence when the push platform 120 is operated to the compressed position, so as to ensure the bone 20 is adequately grinded, sheared, sliced, or cut prior to terminating a rotation or milling of the secondary cutting element 42.

Referring to FIG. 6C, the drive mechanism 212 of the alternative embodiment of the bone grinder 20 may include the gearing system 220. The gearing system 220 may operatively engage the primary cutting element and/or the secondary cutting element 42, thereby rotating the primary cutting element 40 and/or the secondary cutting element 42. The drive mechanism 212 operatively engages the one or more drive shafts 216, with each of the one or more drive shafts operatively engaging at least one of the primary cutting element 40 and/or the secondary cutting element 42. The gearing system 220 may comprise the one or more gears 222, including the first gear 222A corresponding to the primary cutting element 40, the second gear 222B, the third gear 222C, the fourth gear 22D, the fifth gear 222E, and a sixth gear 222F and a seventh gear 222G corresponding to the secondary cutting element 42. For the purpose of the disclosure herein, the first gear 222A, the second gear 222B, the third gear 222C, the fourth gear 222D, the fifth gear 222E, the sixth gear 222F, and the seventh gear 222G may be referred to as the one or more gears 222.

To facilitate the understanding of the embodiments described herein, a number of terms have been defined above. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims. The phrase "in one embodiment," as used herein does not necessarily refer to the same embodiment, although it may.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments of whether these features, elements, and/or states are included or are to be performed in any particular embodiment.

The previous detailed description has been provided for the purposes of illustration and description. Thus, although there have been described particular embodiments of a new and useful BONE GRINDER PROMOTING BONE OSTEOINDUCTIVITY, it is not intended that such references be construed as limitations upon the scope of this disclosure except as set forth in the following claims.

What is claimed is:

1. A method of grinding human bone with a bone grinder, the method comprising:
    loading human bone into a grinding chamber of the bone grinder;
    operatively engaging a primary cutting element and a secondary cutting element via a drive mechanism;
    performing primary cutting operations on the human bone via the primary cutting element of the grinding chamber to produce intermediary bone fragments having an average size ranging from 1000 microns to 6000 microns;
    scraping processed human bone from the primary cutting element via a scraper positioned within the grinding chamber before the primary cutting element;
    directing the intermediary bone fragments from the primary cutting element to the secondary cutting element via an intermediate zone extending from the primary cutting element to a secondary first end of the secondary cutting element, wherein the intermediate zone has first and second walls sloping inward such that a distance between the first and second walls decreases in a generally linear manner from the primary cutting element to the secondary cutting element, and
    replacing osteoinductivity of the intermediary bone fragments by conveying the intermediary bone fragments from the primary cutting element to the secondary cutting element without a swirling motion of the intermediary bone fragments;
    performing secondary cutting operations on the human bone via the secondary cutting element; and
    raking secondary processed human bone from the secondary cutting element via a first rake and second rake positioned within the grinding chamber after the secondary cutting element,
    wherein the secondary cutting element comprises a first cutting tool and a second cutting tool.

2. The method of claim 1, wherein:
    the first cutting tool has a first set of teeth and the second cutting tool has a second set of teeth;
    the first rake including a first set of rake teeth and the second rake including a second set of rake teeth; and
    the step of raking secondary processed human bone further comprises engaging the first set of teeth of the first cutting tool with the first set of rake teeth of the first rake, and engaging the second set of teeth of the second cutting tool with the second set of rake teeth of the second rake.

3. The method of claim 1, wherein:
    the step of performing primary cutting operations further comprises grinding the human bone into the intermediary bone fragments having a size in a range of from 1,000 microns to 6,000 microns.

4. The method of claim 3, wherein:
    the step of performing secondary cutting operations further comprises grinding the intermediary bone fragments into bone powder having a size in a range of from 125 microns to 2,000 microns.

5. The method of claim 1, wherein:
    the step of loading human bone into the grinding chamber includes loading the human bone into a chute positioned before the primary cutting element.

6. The method of claim 5, further comprising:
    moving the human bone toward the primary cutting element via a push platform.

7. The method of claim 1, further comprising:
    pneumatically driving a push platform such that the push platform applies consistent pressure to the human bone.

8. The method of claim 1, wherein:
    the step of scraping processed human bone includes rotating the primary cutting element for a period of time after performing the primary cutting operations; and
    the step of raking secondary processed human bone includes rotating the secondary cutting element for a period of time after performing the secondary cutting operations.

9. The method of claim 1, wherein, following the primary cutting operations, the intermediary bone fragments have an osteoinductivity value, and the step of promoting the osteoinductivity of the intermediary bone fragments comprises no reduction in the osteoinductivity value of the intermediary bone fragments during the conveying of the intermediary bone fragments between the primary cutting element and the secondary cutting element.

10. The method of claim 9, wherein the step of promoting the osteoinductivity of the intermediary bone fragments includes generating insufficient heat to cause any loss in osteoinductivity in the intermediary bone fragments.

11. A method of grinding human bone with a bone grinder, the method comprising:
    loading human bone into a grinding chamber of the bone grinder;
    operatively engaging a primary cutting element and a secondary cutting element via a drive mechanism;
    performing primary cutting operations on the human bone via the primary cutting element of the grinding chamber to produce intermediary bone fragments having an average size ranging from 1000 microns to 6000 microns;
    scraping processed human bone from the primary cutting element via a scraper positioned within the grinding chamber before the primary cutting element;
    directing the intermediary bone fragments from the primary cutting element to the secondary cutting element via an intermediate zone extending from the primary cutting element to a secondary first end of the secondary cutting element, wherein the intermediate zone has first and second walls sloping inward such that a distance between the first and second walls decreases in a generally linear manner from the primary cutting element to the secondary cutting element, and replacing osteoinductivity of the intermediary bone fragments by conveying the intermediary bone fragments from the primary cutting element to the secondary cutting element without a swirling motion of the intermediary bone fragments, such that the osteoinductivity of the intermediary bone fragments is not reduced during the step of conveying the intermediary bone fragments from the primary cutting element to the secondary cutting element;

performing secondary cutting operations on the human bone via the secondary cutting element; and raking secondary processed human bone from the secondary cutting element via a first rake and second rake positioned within the grinding chamber after the secondary cutting element, wherein the secondary cutting element comprises a first cutting tool and a second cutting tool.

12. The method of claim 11, wherein:

the first cutting tool has a first set of teeth and the second cutting tool has a second set of teeth;

the first rake including a first set of rake teeth and the second rake including a second set of rake teeth; and the step of raking secondary processed human bone further comprising engaging the first set of teeth of the first cutting tool with the first set of rake teeth of the first rake, and engaging the second set of teeth of the second cutting tool with the second set of rake teeth of the second rake.

13. The method of claim 11, wherein the bone grinder comprises a push platform, the method further comprising:

pneumatically driving the push platform such that the push platform applies consistent pressure to the human bone.

14. The method of claim 11, wherein:

the step of scraping processed human bone includes rotating the primary cutting element for a period of time after grinding the human bone into intermediary bone fragments; and the step of raking secondary processed human bone includes rotating the secondary cutting element for a period of time after grinding the intermediary bone fragments into bone powder.

15. A method of grinding human bone with a bone grinder, the method comprising:

loading human bone into a grinding chamber of the bone grinder via a chute;

moving the human bone through the chute and toward a primary cutting element via a push platform;

operatively engaging the primary cutting element and a secondary cutting element via a drive mechanism;

grinding the human bone into intermediary bone fragments having a size in a range of from 1,000 microns to 6,000 microns via the primary cutting element;

scraping processed human bone from the primary cutting element via a scraper positioned within the grinding chamber before the primary cutting element;

directing the intermediary bone fragments from the primary cutting element to the secondary cutting element via an intermediate zone extending from the primary cutting element to a secondary first end of the secondary cutting element, wherein the intermediate zone has first and second walls sloping inward such that a distance between the first and second walls decreases in a generally linear manner from the primary cutting element to the secondary cutting element, replacing osteoinductivity of the intermediary bone fragments by conveying the intermediary bone fragments from the primary cutting element to the secondary cutting element without a swirling motion of the intermediary bone fragments such that insufficient heat is generated during the step of conveying the intermediary bone fragments from the primary cutting element to the secondary cutting element to cause any loss in osteoinductivity in the intermediary bone fragments;

grinding the intermediary bone fragments into bone powder having a size in a range of from 125 microns to 2,000 microns via the secondary cutting element; and raking secondary processed human bone from the secondary cutting element via a first rake and second rake positioned within the grinding chamber after the secondary cutting element, wherein the intermediate zone is configured to prevent swirling of the intermediary bone fragments between the primary cutting element and the secondary cutting element, wherein the secondary cutting element comprises a first cutting tool and a second cutting tool.

* * * * *